United States Patent
Yamada

(10) Patent No.: US 8,922,784 B2
(45) Date of Patent: Dec. 30, 2014

(54) LIGHT SOURCE APPARATUS AND IMAGE PICKUP APPARATUS USING THE SAME

(75) Inventor: Tomohiro Yamada, Yokohama (JP)

(73) Assignee: Canon Kabushiki Kaisha, Tokyo (JP)

( * ) Notice: Subject to any disclaimer, the term of this patent is extended or adjusted under 35 U.S.C. 154(b) by 208 days.

(21) Appl. No.: 12/942,731

(22) Filed: Nov. 9, 2010

(65) Prior Publication Data

US 2011/0134433 A1 Jun. 9, 2011

(30) Foreign Application Priority Data

Dec. 9, 2009 (JP) ................................. 2009-279912

(51) Int. Cl.
*G01B 9/02* (2006.01)
(Continued)

(52) U.S. Cl.
CPC ........ *H01S 5/146* (2013.01); *G01N 2021/1787* (2013.01); *H01S 5/4025* (2013.01); *H01S 3/1121* (2013.01); *H01S 3/136* (2013.01); *A61B 5/0088* (2013.01); *G01N 21/4795* (2013.01); *A61B 5/0073* (2013.01); *A61B 2562/0242* (2013.01); *H01S 3/1312* (2013.01); *H01S 3/1109* (2013.01); *H01S 2301/04* (2013.01); *A61B 5/0066* (2013.01); *A61B 5/0062* (2013.01)
USPC ....................................................... 356/497

(58) Field of Classification Search
CPC ........... G01B 9/02004; G01B 9/02091; A61B 5/0066; A61B 5/0073; G01N 21/4795; G01N 2021/1787; H01S 2301/04; H01S 3/1109; H01S 3/1121; H01S 3/1312
USPC ........... 372/20, 28, 29.011, 32, 44.01, 93, 19, 372/26, 43.01, 68, 92, 94, 29.02, 9, 18, 23, 372/29.01, 38.07, 38.02; 356/479, 480, 356/484, 485, 486, 487, 489, 496, 497, 498, 356/511; 359/341, 341.5, 342, 344, 346; 257/98
See application file for complete search history.

(56) References Cited

U.S. PATENT DOCUMENTS 4,680,769 A * 7/1987 Miller ......................... 372/50.22
6,665,320 B1 12/2003 Arbore et al.
(Continued)

FOREIGN PATENT DOCUMENTS

CN 101518440 A 9/2009
JP 6-090050 A 3/1994
(Continued)

OTHER PUBLICATIONS

Yamashita, et al., "Wide and Fast Wavelength-tunable mode-locked fiber laser based on dispersion tuning", Opt. Exp.vol. 14, No. 20, pp. 9299-9306, 2006.

(Continued)

*Primary Examiner* — Michael A Lyons
*Assistant Examiner* — Rufus Phillips
(74) *Attorney, Agent, or Firm* — Canon USA Inc. IP Division

(57) ABSTRACT

A light source apparatus includes an optical resonator provided with a plurality of gain media that amplify light and an optical waveguide and a control unit configured to individually control amplification factors of the plurality of gain media, in which the plurality of gain media have mutually different maximum gain wavelengths whose amplification regions are mutually partially overlapped, and a wavelength at which a total gain by the plurality of gain media becomes a maximum value is set to be variable on the basis of the control on the amplification factors.

25 Claims, 18 Drawing Sheets

(51) Int. Cl.
   *H01S 5/14* (2006.01)
   *A61B 5/00* (2006.01)
   *G01N 21/17* (2006.01)
   *H01S 5/40* (2006.01)
   *H01S 3/11* (2006.01)
   *H01S 3/136* (2006.01)
   *G01N 21/47* (2006.01)
   *H01S 3/131* (2006.01)

(56) References Cited

U.S. PATENT DOCUMENTS

| | | |
|---|---|---|
| 7,414,779 B2 * | 8/2008 | Huber et al. .................. 359/333 |
| 2006/0187537 A1 | 8/2006 | Huber |

FOREIGN PATENT DOCUMENTS

| | | |
|---|---|---|
| JP | H07-045889 A | 2/1995 |
| JP | 2007-115900 A | 5/2007 |
| JP | 2007-184557 A | 7/2007 |

OTHER PUBLICATIONS

Nakazaki, et al., "Fast and wide tuning range wavelength-swept fiber laser based on dispersion tuning and its application to dynamic FBG sensing", Optics Express, May 11, 2009, pp. 8310-8318, vol. 17, No. 10.

* cited by examiner

LIGHT SOURCE APPARATUS AND IMAGE PICKUP APPARATUS USING THE SAME

BACKGROUND OF THE INVENTION

1. Field of the Invention

The present invention relates to a light source apparatus capable of changing an oscillation wavelength and an image pickup apparatus using the same.

2. Description of the Related Art

A variety of light sources, in particular, laser light sources, which are capable of changing an oscillation wavelength have been utilized in a communication network field and a field of an inspection apparatus.

In the communication network field, a high-speed wavelength switching is demanded, and also, in the field of an inspection apparatus, a high-speed broadband wavelength sweeping is demanded.

Use applications of a wavelength-variable (sweeping) light source in the inspection apparatus include a laser spectrometer, a dispersion measurement device, a film thickness measurement device, a swept source optical coherence tomography (SS-OCT) apparatus, and the like.

The optical coherence tomography (hereinafter, which will also be referred to as OCT) is configured to pick up a tomographic image of a sample by using an optical low-coherence interference, and this is an image pickup technology whose research in a medical field has been activated in recent years because a micron-order spatial resolution can be obtained, a noninvasive property is attained, and the like.

Currently, the OCT is used for an image pickup in eye clinics, an image pickup in dental clinics, or the like as a resolution in a depth direction is set as several microns and also a tomographic image up to a depth of several mm can be obtained.

The SS-OCT is designed to temporally sweep an oscillation wavelength (frequency) of a light source and falls within a category of a Fourier domain (FD) OCT. A spectrum domain (SD) OCT that also falls within the category of the FDOCT needs a spectrometer for dispersing an interference light, but the SS-OCT is also expected to obtain an image in which a loss of a light amount is small and an SN ratio is high as the spectrometer is not used.

In a case where a medical-use image pickup apparatus is composed by using a wavelength sweeping light source, a period of time for obtaining an image can be shortened as a sweeping speed is faster, and the apparatus is suitable to a vital observation (so-called, in situ-in vivo imaging) in which a biomedical tissue is not collected from a living body and the biomedical tissue is directly observed.

Also, as a sweeping band of the wavelength is wider, the spatial resolution of the tomographic image can be increased.

To be more specific, a depth resolution is represented by the following expression (1) while the wavelength sweeping width is set as $\Delta\lambda$, and an oscillation wavelength is set as $\lambda 0$.

Expression 1

$$\frac{2\ln 2}{\pi} \times \frac{\lambda_0^2}{\Delta\lambda} \quad (1)$$

Therefore, in order to increase the depth resolution, an expansion of the wavelength sweeping width $\Delta\lambda$ is needed.

For the wavelength sweeping light source used in the SS-OCT, one based on a dispersion tuning system which is developed in a communication band is disclosed in Yamashita, et al. Opt. Exp. Vol. 14, pp. 9299-9306 (2006) (hereinafter, which will be referred to as "Non-patent Document 1").

In this dispersion tuning system, by utilizing a state in which a free spectral range (FSR) of the resonator has a wavelength dependence, the oscillation wavelength in an active mode-lock state is controlled. At this time, the wavelength sweeping is performed by changing a frequency of a modulation signal that may cause a mode-lock. In other words, by sweeping a mode-lock frequency, the central wavelength at the time of the mode-lock is swept. For this reason, in order to perform a high-speed wavelength sweeping, it is necessary to change the frequency of the modulation signal at a high speed.

The FSR indicates a frequency interval in a resonator mode with respect to light circulating in the resonator and is represented by the following expression (2) while the light speed in vacuum is set as c, a refractive index of the resonator is set as n, and a resonator length is set as L.

Expression 2

$$FSR = \frac{c}{nL} \quad (2)$$

Also, according to Non-patent Document 1, in the dispersion tuning system, a wavelength sweeping range is represented by the following expression (3).

Expression 3

$$\Delta\lambda = \frac{n}{cDN} \quad (3)$$

Where n denotes the refractive index of the resonator, D denotes a dispersion parameter of the resonator, and N denotes an order (natural number) of the mode-lock.

Also, aside from this, for a purpose of an optical wavelength division multiplexing, a mode-lock laser technology for constructing an apparatus provided with a plurality of gain materials in a resonator and carrying out pulse oscillations in a plurality of spectrum bands at the same time is proposed in Japanese Patent Laid-Open No. 6-90050 (hereinafter, which will be referred to as "Patent Document 1").

According to the dispersion tuning system based on the active mode-lock disclosed in the above-described Non-patent Document 1, the wavelength sweeping can be performed, but the sweeping range is limited to a relatively narrow range in principle, and also the sweeping speed is not necessarily sufficient. Also, wavelength sweeping notches at the time of the sweeping are not constant as the FSR has the wavelength dependence, and in order to obtain a quasi-smooth sweeping, a devise on a detection side is demanded.

On the other hand, according to the laser apparatus disclosed in Patent Document 1, oscillations at a plurality of wavelengths can be carried out, but it is simply assumed that the oscillations are carried out at a plurality of wavelengths at the same time point, and an intention of performing the wavelength sweeping does not exist.

Furthermore, for the wavelength sweeping light source, one using the above-described pulse light source and also one using CW light (continuous wave: continuous wave oscillation light) are conceivable, but a light source having a wide sweeping range and a sufficiently high sweeping speed is not obtained in an actual situation.

SUMMARY OF THE INVENTION

The present invention provides a light source apparatus including: an optical resonator provided with a plurality of gain media that amplify light and an optical waveguide; and a control unit configured to individually control amplification factors of the plurality of gain media, in which the plurality of gain media have mutually different maximum gain wavelengths whose amplification regions are mutually partially overlapped, and a wavelength at which a total gain by the plurality of gain media becomes a maximum value is set to be variable on the basis of the control on the amplification factors.

The present invention encompasses an optical tomographic image pickup apparatus. An optical tomographic image pickup apparatus according to an embodiment of the present invention includes the a light source unit using light source apparatus according to the embodiment of the present invention, a sample measurement unit configured to irradiate a sample with light from the light source unit and transmit reflected light from the sample, a reference unit configured to irradiate a reference mirror with the light from the light source unit and transmit reflected light from the reference mirror, an interference unit configured to interfere the reflected light from the sample measurement unit and the reflected light from the reference unit, a light detection unit configured to detect interference light from the interference unit, and an image processing unit configured to obtain a tomographic image of the sample on the basis of light detected by the light detection unit.

The light source apparatus according to the embodiment of the present invention includes a plurality of gain media having mutually different maximum gain wavelengths whose amplification regions are mutually partially overlapped and a control unit configured to individually control the plurality of gain media. Then, a wavelength at which a total gain by the plurality of gain media becomes a maximum value is set to be variable on the basis of the control on the amplification factors.

With this configuration, by appropriately selecting the plurality of gain media having mutually different maximum gain wavelengths, it is possible to sweep the wavelength of the desired band width. Then, as the gain media are controlled by the individual control units, it is possible to sweep the maximum wavelength of the total gain by the plurality of gain media at a desired speed.

Also, according to the embodiment of the present invention, it is possible to provide a light source capable of performing a wide band wavelength sweeping only depending on a band width of the gain in the CW oscillation. Also, it is possible to set wavelength sweeping notches to be substantially constant.

The light source apparatus according to the embodiment of the present invention can realize a stable mode-lock state and perform the wavelength sweeping in the case of the pulse oscillation. Also, even in a case where the sweeping of the oscillation wavelength is performed in the mode-lock state, a restriction of the wavelength sweeping range due to the wavelength dispersion which is seen in the dispersion tuning system is eliminated, and it is possible to perform the sweeping of the oscillation wavelength in a wide band.

Further features of the present invention will become apparent from the following description of exemplary embodiments with reference to the attached drawings.

DESCRIPTION OF THE EMBODIMENTS

Hereinafter, embodiments of the present invention will be described with reference to the drawings.

Figure 1:
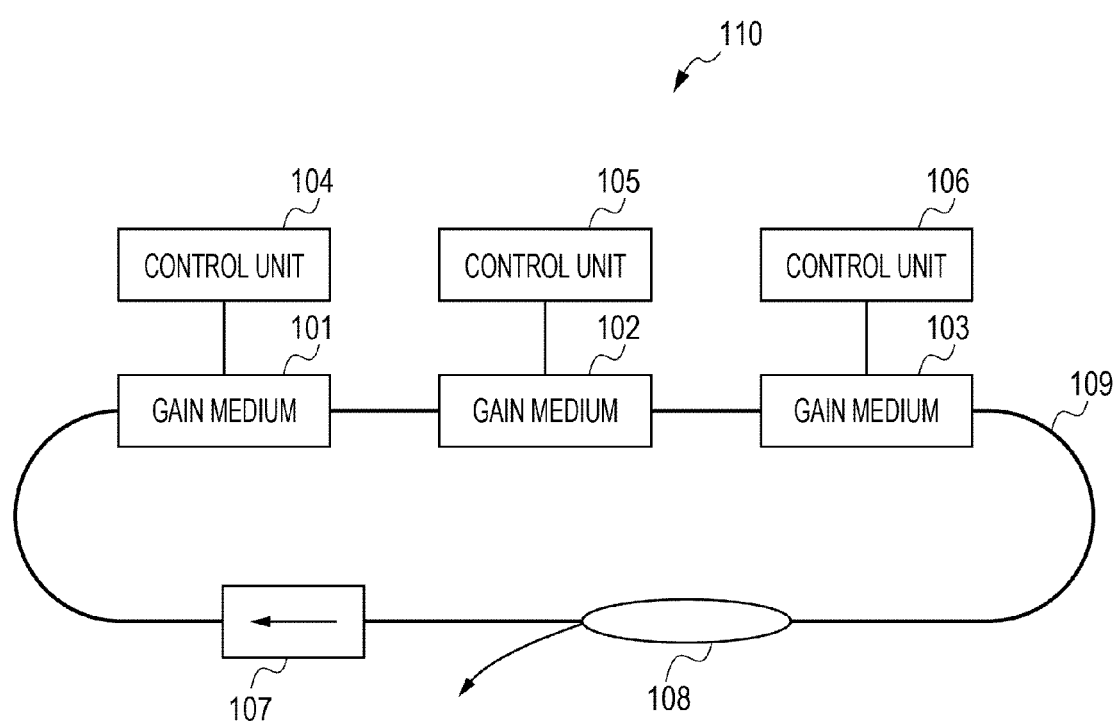
FIG. 1 is a schematic drawing illustrating an example of a light source apparatus of the present invention.

FIG. 1 is a schematic drawing illustrating an example of a light source apparatus of the present invention.

In FIG. 1, a light source 110 includes a plurality of gain media 101, 102, and 103 that amplify light and also control units 104, 105, and 106 that individually control amplification factors (gain) of these gain media. These gain media for the light are optically coupled via an optical waveguide 109 to a coupler 108 and an isolator 107 and form a ring-type optical resonator. The isolator is arranged for a purpose of suppressing a generation of a spatial distribution of a gain by a standing wave which is generated in the gain medium by causing light in a ring-type optical resonator to circulate in one direction. According to the invention of the present application, the optical resonator is not limited to the ring-type optical resonator, but herein, an example of using the ring-type optical resonator will be described.

For the gain media 101, 102, and 103 for the light, for example, a semiconductor optical amplifier (SOA) can be used. The semiconductor optical amplifier is basically for utilizing a gain mechanism of the light while the resonator is removed from the semiconductor laser and has a configuration of suppressing a reflection on an end face so as not to construct a resonator. Herein, for the gain medium (amplification medium) of the light, the semiconductor optical amplifier is used as an example for the description.

Figure 2:
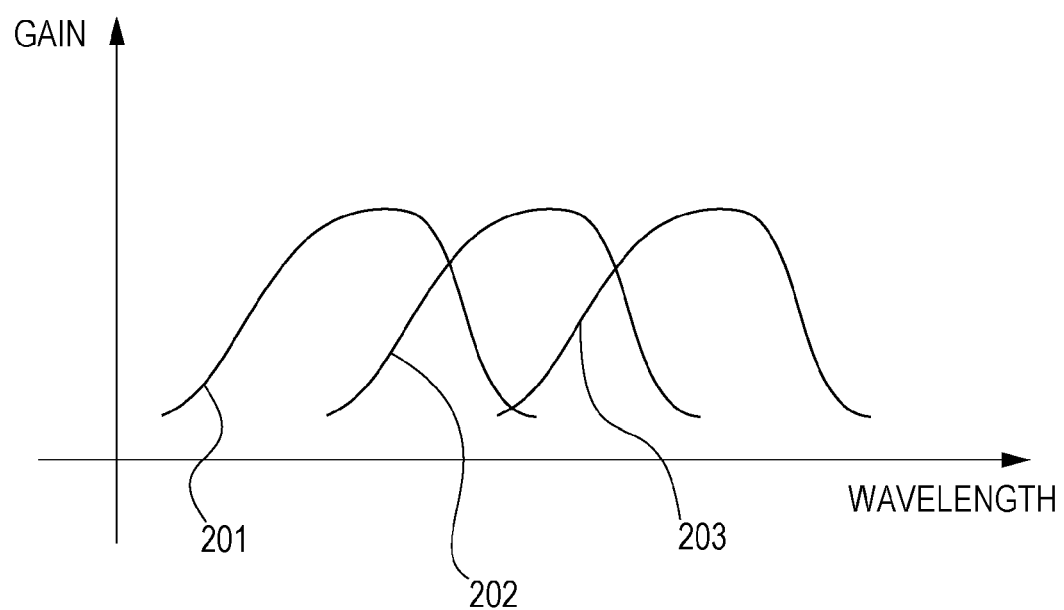
FIG. 2 is a graph representing a relation between a gain and a wavelength of a gain medium constituting the light source apparatus according to the present invention.

The gain medium 101 has a gain spectrum (gain curve) 201, the gain medium 102 has a gain spectrum 202, and the gain medium 103 has a gain spectrum 203. In other words, the gain media are configured to have different maximum gain wavelengths (gain peaks) as illustrated in FIG. 2 and also parts of amplification regions thereof mutually overlap.

Figure 3:
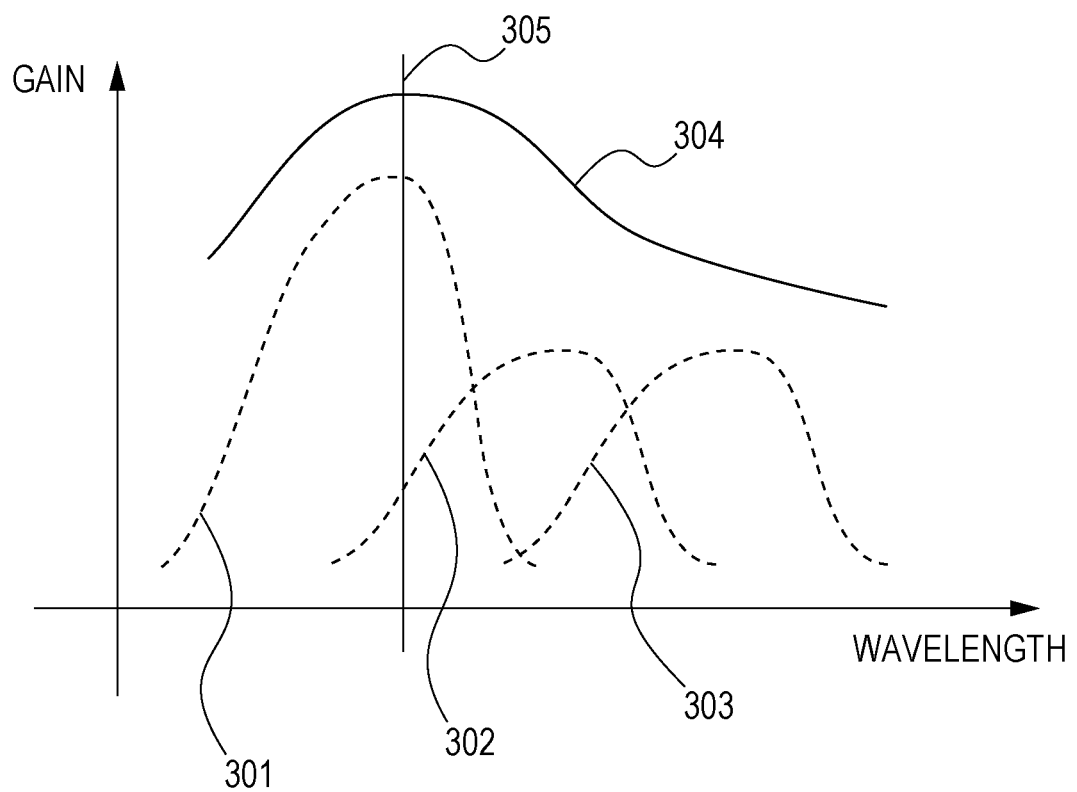
FIG. 3 is a graph representing a relation between a total gain and a spectrum obtained by the light source apparatus according to the present invention.

In this state, by using the control units 104 to 106, the amplification factors (gain) of the gain media 101 to 103 are individually (for example, periodically) controlled. For example, as illustrated in FIG. 3, by setting a gain spectrum 301 of the gain medium 101 larger than a gain spectrum 302 of the gain medium 102 or a gain spectrum 303 of the gain medium 103, a profile (gain curve, gain property) of a total gain by the plurality of gain media is like a total gain 304.

The semiconductor optical amplifier can control the gains (amplification factors) on the basis of a control on a current injection amount. In view of this, by temporally (periodically) changing injection currents injected into the plurality of gain media for amplifying the light, a total gain peak can be changed temporally (periodically) as will be described below.

The light source apparatus according to the embodiment of the present invention can be constructed by using both an apparatus performing a continuous oscillation (Continuous Wave, CW) operation and an apparatus performing a pulse oscillation operation. First, the apparatus performing the continuous oscillation will be described.

The light source apparatus illustrated in FIG. 1 oscillates at the continuous wave (CW). If the loss of the light does not have much wavelength dependence, the oscillation wavelength is basically in the vicinity of the wavelength of the resonator mode closest to the wavelength at which the gain becomes the maximum value and is an oscillation wavelength 305 in FIG. 3.

In the light source apparatus according to the embodiment of the present invention, the maximum gain wavelengths that the plurality of gain media have are mutually different, and by changing the individual gains (amplification factors) of the gain media, it is possible to change the wavelength at which the gain becomes the maximum value (gain peak).

Time changes in gains (amplification factors) related to the plurality of gain media 101 to 103 will be described with reference to FIG. 4 and FIG. 5.

Figure 4:
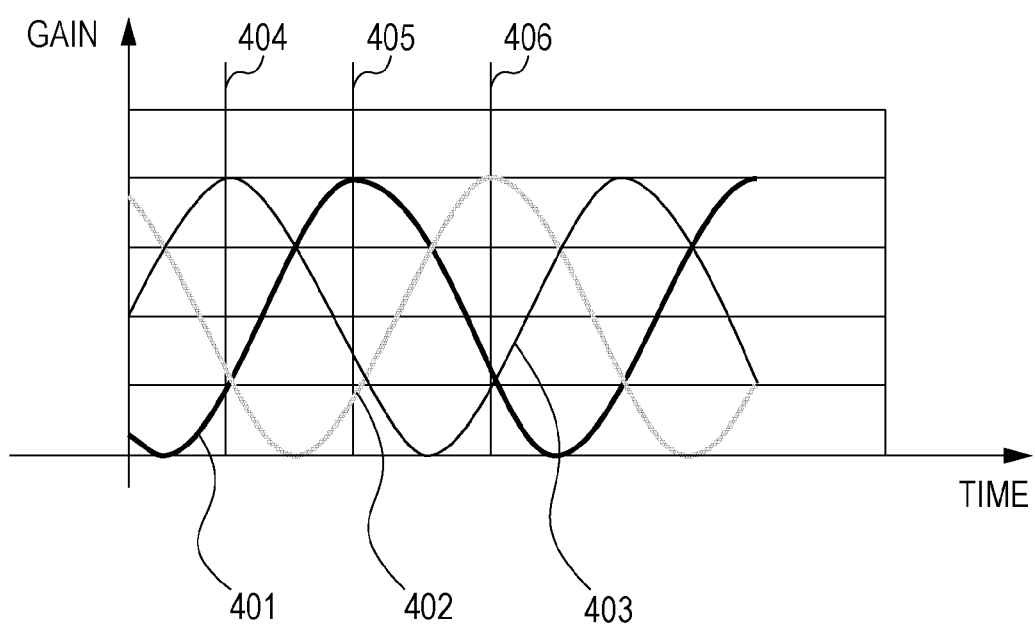
FIG. 4 is a graph representing a relation between a gain and a spectrum obtained by a light source apparatus according to an embodiment.

In FIG. 4, reference numeral 401 represents a time change in the gain of the gain medium 101 in FIG. 1, 402 represents a time change in the gain of the gain medium 102, and 403 represents a time change in the gain of the gain medium 103.

Figure 5:
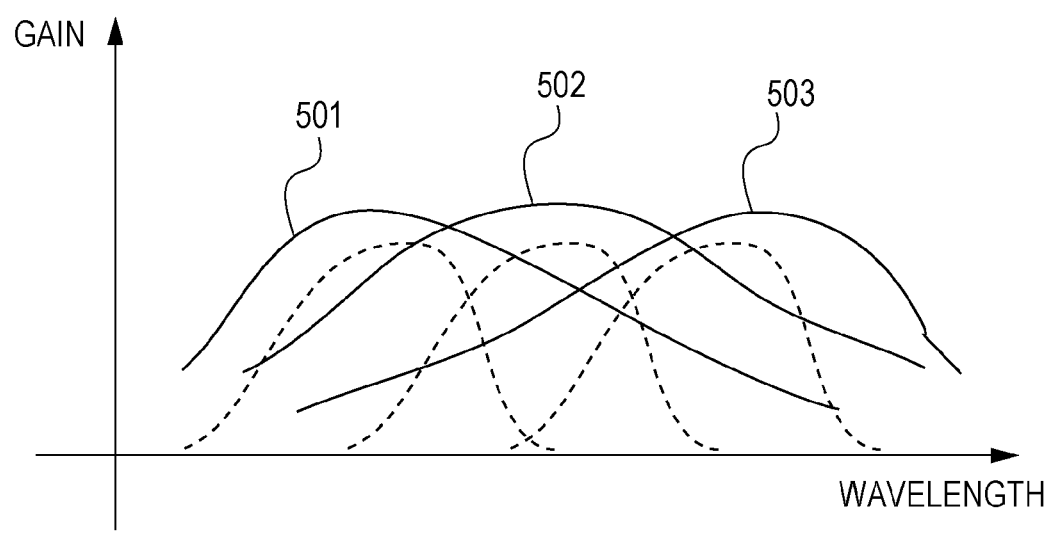
FIG. 5 is a graph representing a relation between a total gain and a spectrum obtained by the light source apparatus according to the present invention.

As illustrated in FIG. 4, when the gain of the gain media are controlled, at a time point 404, a total gain 501 illustrated in FIG. 5 is obtained, at a time point 405, a total gain 502 is obtained, and at a time point 406, a total gain 503 is obtained.

As understood from FIG. 4 and FIG. 5, along with the time change, the gain 401, the gain 402, and the gain 403 change, and total gain peaks obtained by overlapping the three gains (maximum gain wavelengths) change into the total gains 501, 502, and 503. Then, while following the changes of the total gain peaks, the continuous oscillation wavelength of the light source apparatus also changes.

Thus, in the light source apparatus according to the embodiment of the present invention, by individually changing the gains (amplification factors) of the plurality of gain media, the total gain obtained by overlapping the gain curves of the plurality of gain media is changed, and it is possible to temporally change the oscillation wavelength of the continuous oscillation. It is noted that in FIG. 4, a sine wave is illustrated as a signal for performing the temporal wavelength sweeping, but the signal waveform is not limited to this.

At this time, while the oscillation wavelength at a certain instance is maintained uniform, in order to temporally sweep the oscillation wavelength, while a shape of the total gain spectrum maintains a single-peak property, the maximum wavelength (peak) preferably smoothly shifts. For that purpose, the gain bands of the respective gain media need to be overlapped. This is because if a gain medium having a spectrum band not overlapped with any amplification regions exists, the oscillation wavelength (central wavelength) in the relevant spectrum band becomes discrete.

Then, the overlap of the mutual gain bands of the respective gain media is preferably sufficiently large.

The gain bands preferably configured in such a manner that with respect to the adjacent gain media, the wavelength regions respectively constituting a full width at half maximum (FWHM) are partially overlapped.

Furthermore, in order to set the profile of the total gain to have the single peak property, the gain spectrums of the individual gain media also preferably have the single peak property.

Also, in order to making it possible to set the maximum wavelength of the total gain (gain peak) to be an arbitrary wavelength between the maximum values of the individual gain spectrums that the plurality of gain media have, the individual gains (amplification factors) that the plurality of gain media have and these ratios are preferably adjustable.

According to the invention of the present application, the example in which the number of the plurality of gain media is three has been described, but the number of gain media is not particularly limited as long as the number is plural. However, when the size of the light source apparatus, the smoothness of the wavelength sweeping, and the like are taken into account, the number of the gain media is set in a range between 2 and 20 in general, more preferably, between 3 and 10, and most preferably, between 3 and 5.

Herein, when a consideration is given of a case in which a total number N of gain media are used and the sweeping of the maximum wavelength of the total gain (peak) is carried out at a period T1, in order to carry out the smooth change in the peak wavelength of the total gain, among the gains applied to the light from the respective gain media for amplifying the adjacent frequency bands, a phase difference $\Delta\phi$ of the gains having a component of the period T1 is preferably set as $2\pi/N$.

In addition to this, in particular, in a case where the wavelength sweeping is performed at a high speed, a time $\tau$ used for the light to propagate in the resonator between the adjacent gain media is taken into account, and it is necessary to add a phase difference $2\pi\tau/T1$ to a drive control on the adjacent gain media. It is however noted that in a case where the time used for the wavelength sweeping is extremely larger as compared with the time used for the light to circulate in the resonator or a case where a distance between the gain media is sufficiently close, a term $2\pi\tau/T1$ may be ignored.

Also, the period of the wavelength sweeping is preferably in synchronism with the period for the light to circulate in the resonator or is preferably a reciprocal of an integer of a time used for the light to circulate a round (one round) in the resonator. That is, this is equivalent to Fourier domain mode-locking.

FDML refers to an operation mode in which as the period of the wavelength sweeping is synchronized with the period in which the light circulates in the resonator, when the amplified spontaneous emission light which is amplified by the total gain at a certain time point circulates in the resonator and returns to the gain material again, the light is amplified by the gain material having the total gain with the same profile once again.

By performing such an ASE light amplification operation by the sufficient number of circulating times, the intensity of the ASE light is amplified, and eventually it is possible to construct the light source having the high intensity and the wavelength at which the intensity of the ASE spectrum becomes the largest changes at a high speed. This is an outline of the FDML.

In other words, in the FDML, it is necessary to set the modulation period of the maximum wavelength of the total gain as a reciprocal of an integer of a time used for the ASE light to circulate one round in the resonator.

In a case where the FDML operation is performed by the light source according to the embodiment of the present invention, a wavelength-variable filter is not needed, and therefore it is possible to realize the high-speed wide-band light source without a rate controlling by the operation speed of the wavelength-variable filter or the wavelength range.

As will be described below, for a general mode-lock operation, the wavelength at which the gain becomes the maximum value does not need to change with the time. By simply varying the size of the total gain itself with the time or providing an optical modulator in the optical resonator and changing a transmittance of the relevant optical modulator, the loss in the optical resonator may be changed temporally. At this time, it is necessary to set a modulation period of the size of the total gain or a modulation period of the optical modulator as a reciprocal of an integer of the time in which the light circulates in the resonator.

In contrast to this, in the FDML, with the time, the wavelength at which the gain becomes the maximum value is varied temporally. Then, it is necessary to set the modulation period of the wavelength at which the gain becomes the maximum value as a reciprocal of an integer of the time in which the light circulates in the resonator.

This is a difference between the FDML and the general mode-lock operation.

In the configuration of the light source according to the embodiment of the present invention, in the continuous oscillation state, the oscillation at a desired wavelength can be performed, and also the oscillation wavelength can be temporally swept.

Also, by matching the period of the wavelength sweeping with the time in which the light circulates in the resonator, the loss with respect to the light in the resonator is suppressed to a low level, and it is possible to realize the highly efficient light source. Furthermore, by controlling the phase difference of the time fluctuations in the gain of the plurality of gain materials, the smooth wavelength sweeping can be carried out.

According to the invention of the present application, for an optical gain medium, a rare-earth added (ion-doped) optical fiber containing erbium, neodymium, or the like, one added with pigment in the optical fiber for performing the amplification by the pigment, the semiconductor optical amplifier, and the like can be used. The rare-earth added optical fiber is preferably used for obtaining a high gain and a satisfactory noise characteristic. With regard to the pigment-added optical fiber, by appropriately selecting a fluorescence pigment material or a host material thereof, the number of selections of the wavelengths is increased, and it is possible to increase the degree of freedom for the settings of the amplification region as the gain medium and the gain profile.

The semiconductor optical amplifier is small and also can perform the high speed control, and is preferably used in terms of the individual control on the amplification factors of the plurality of gain media (gains). For the semiconductor optical amplifier, both the resonator type optical amplifier and a travelling wave amplifier can be used. For a material constituting the semiconductor optical amplifier, a compound semiconductor or the like constructing a general semiconductor laser can be used, and to be more specific, InGaAs-based, InAsP-based, GaAlSb-based, GaAsP-based, AlGaAs-based, and GaN-based compound semiconductors and the like can be exemplified.

According to the invention of the present application, the optical waveguide can be basically used as long as a function of propagating the like is provided, but in order to suppress an influence from the outside as much as possible, a slab waveguide for containing the light to be propagated or optical fiber is preferably used.

The waveguide for containing the light to be propagated basically has a part with a high refractive index (core) and a part with a low refractive index (clad), and in order to propagate the light at a relatively long distance, an optical fiber is preferably used. For the optical fiber, an optical fiber using quartz ($SiO_2$) glass, an optical fiber using plastic, an optical fiber using both quartz and plastic, and the like can be exemplified.

When a focus is on a function aspect of the optical fiber, for example, a polarization maintaining fiber or a single mode fiber is preferably used. The polarization maintaining fiber is preferably used because a polarization state in the optical waveguide is easily held, and the polarization maintaining fiber is resistant to a disturbance from the outside. Also, the single mode fiber is a low cost, and further, a benefit is provided in which a polarization beat or the like is hardly caused as a birefringence does not exist internally.

For the optical waveguide, it is also possible to adopt an optical waveguide having zero group velocity dispersion with respect to the wavelengths of the amplification regions of the plurality of gain media.

According to the invention of the present application, a control unit is capable of individually controlling the amplification factors of the optical gain medium, and it includes a signal control unit capable of temporally changing a current signal injected into a semiconductor optical gain medium in a case where the semiconductor optical amplifier is used for the optical gain medium.

The signal control unit can be constructed by a circuit that, for example, monitors the light actually output from the light source according to the embodiment of the present invention and can control the current signals of the plurality of gain media so as to set the wavelength of the outgoing light as a desired wavelength (unit configured to send the control signals).

Such circuit and control will be described more specifically below.

In a simplest example, for example, like a function generator, the circuit provided with a current source for generating an arbitrary signal waveform and a delay circuit for adding a constant phase difference on this signal and configured to introduce a temporal phase difference to a change in the amplification factor for each gain medium by adding the delay amount at different values for each of the gain media is exemplified.

For a more precise control, the circuit that may detect the oscillation wavelength by using a spectral unit such as a spectrometer for monitoring the oscillation wavelength, change the currents flowing into the respective optical gain media in a case where the oscillation wavelength is out of the desired value, and change the control current so that the oscillation at the desired central wavelength is carried out is exemplified.

For example, in a case where the actual oscillation wavelength is deviated on a short wavelength side with respect to the desired oscillation wavelength, the current values flowing to the respective gain media may be controlled so that the peak of the total gain is moved to a long wavelength side. Also, a control may be performed so that the total gain is shifted to the long wavelength side by increasing the current flowing to the optical gain medium having the maximum wavelength of the gain on the long wavelength side with respect to the current oscillation wavelength and on the other hand by reducing the current flowing to the optical gain medium having the maximum wavelength of the gain on the short wavelength side with respect to the current oscillation wavelength.

Even in a case where such a feed back control is not included, as a correspondence relation among the current values flowing to the respective optical gain media, the spectrum information on the total gain accompanied by this, and further the oscillation wavelength at the total gain is held as a table, the control on the oscillation wavelength can be performed by appropriately reading desired data from this table.

Next, the light source of the pulse oscillation operation will be described.

In the light source apparatus according to the embodiment of the present invention, even in the case of a pulse oscillation in a mode-lock (mode synchronization, phase synchronization) state, the oscillation wavelength is variable. The mode-lock means that a large number of simultaneously oscillating vertical mode phases are synchronized. In the case of a laser oscillation having an inhomogeneous broad, the oscillations are caused at a large number of frequencies (resonator mode). At this time, the phases of the respective frequencies are not matched and are temporally fluctuated (as a result of an interference of the respective modes, outputs are also fluctuated). On the basis of the mode-lock, the pulse in which the peak power is large and the pulse width is extremely narrow is obtained.

The mode-lock is roughly divided into an active mode-lock and a passive mode-lock.

Figure 6:
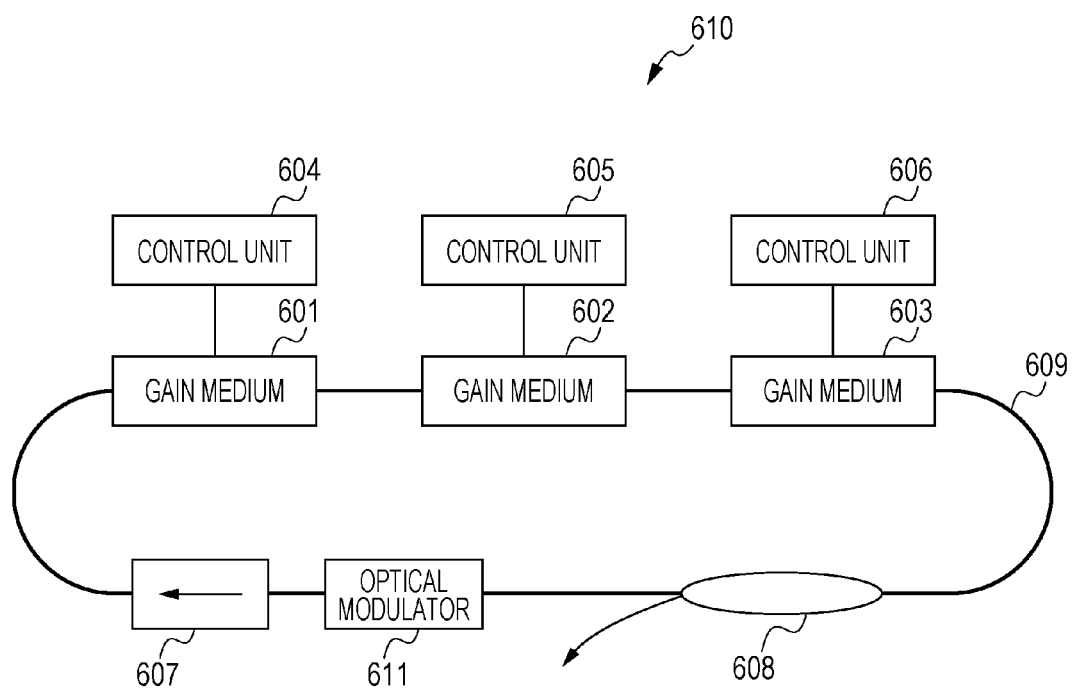
FIG. 6 is a graph representing a relation between a total gain and a spectrum obtained by the light source apparatus according to the present invention.

FIG. 6 is a schematic diagram illustrating an example of the light source apparatus using the active mode-lock, which is an example where an optical modulator 611 is incorporated in the resonator of FIG. 1.

The active mode-lock (mode synchronization) refers to a method of synchronizing the respective modes by incorporating the optical modulator in the resonator and providing an electric signal to the optical modulator. According to this method, a plurality of modes are simultaneously excited (vertical multiple mode oscillations), and when these phase relations are set to be uniform, the laser performs a high frequency pulse oscillation operation.

For the vertical multiple mode oscillations and the phase relation fixing between the modes, typically, a nonlinearity is provided in the optical system of the laser, and also some optical modulator is introduced.

For the optical modulator, one utilizing an electro-optical effect, one utilizing an acoustic (or ultrasonic wave) optical effect, one utilizing an electroabsorption effect of the semiconductor, and the like can be utilized. For the stable drive of the pulse, for example, a supersaturated absorber mirror or the like can be used. Furthermore, instead of newly providing the optical modulator, a signal for originally controlling in the optical modulator may be overlapped on an amplification factor control signal applied to the optical gain medium (for example, SOA) itself.

For example, in a case where the optical modulator is a transmittance control type optical modulator, by varying the transmittance to the high frequency by the optical modulator, a sideband is excited on the low frequency side and the high frequency side of the firstly excited resonator mode. In a case where a frequency applied from the optical modulator is set as $\omega'$, when the frequency of the firstly excited resonator mode is set as $\omega 0$, the sideband is excited at a frequency of $\omega 0 \pm \omega'$.

At this time, if $\omega'$ is equal to the resonator mode interval or an integral multiple of this, the sideband excites the resonator mode next to $\omega 0$. In this manner, the mutual resonator modes excite via the sideband, and the vertical multiple mode oscillations can be realized.

In other words, it is necessary to set the frequency for driving the optical modulator to be equal to an integral multiple of the free spectral range that the ring resonator has.

In this case, the following expression (4) is established.

$$F = c/nL \qquad \text{Expression (4)}$$

Herein, F denotes a free spectral range, c denotes a light speed in vacuum, n denotes a refractive index with respect to the light circulating in the ring resonator, and L denotes a circumferential length of the ring resonator.

Also, by introducing the nonlinearity that the gain material, the nonlinear material, or the optical modulator itself has into the resonator, a mutual action between the modes is caused, and a phase relation between the modes is decided. As a result, the laser oscillates and outputs the pulse string.

Therefore, when the active mode-lock is applied, if the resonator mode interval does not have the frequency dependency or the frequency dependency is extremely small, with the above-described mechanism, almost all the resonator modes in the gain band are excited, and the mode synchronization can be applied.

Also, as another mode, in a case where the spectrum shape of the total gain is changed, if the wavelength dependence or the FSR of the ring resonator is small in the spectrum band of the total gain that may be generated, even when the total gain is changed, the modulation frequency is not changed because of the mode synchronization. Without changing the modulation frequency of the above-described optical modulator, the mode synchronization state is maintained. In other words, if the gain profile is changed while the drive frequency for the optical modulator is fixed, the change or sweeping of the oscillation wavelength can be performed in the mode synchronization state as it is.

For example, when the length of the ring resonator is set as ~200 m and the refractive index is set as ~1.5, the optical circumferential length of the ring resonator is approximately 300 m, and the light propagating therein circulates at ~1 MHz in the resonator. Therefore, the resonator mode interval (free spectral range: FSR) of this resonator is also set as ~1 MHz. In view of the above, the mode-lock (synchronization) can be applied if the drive frequency for the optical modulator is set as 1 MHz or an integral multiple of this. In this state, a pulse string equal to the drive frequency for the optical modulator, in other words, a repetition frequency of 1 MHz or an integral multiple of this is generated.

The center of the oscillation wavelength in the mode-lock (synchronization) oscillation is also where the gain is basically the maximum spectrum band, and therefore the oscillation wavelength is in the vicinity of the wavelength at which the total gain (gain) becomes the maximum value.

In other words, similarly as in the case of the above-described CW oscillation, when the total gain is set, for example, as illustrated in FIG. 3 on the basis of the control of the control unit (control drive unit) for individually controlling the amplification factors of the plurality of gain media, the central frequency in the mode-lock oscillation can also be set in the vicinity of the oscillation wavelength 305 at which the total gain becomes the maximum value.

Also, as described above, as the maximum gain wavelengths that the plurality of gain media have are mutually different, by changing the individual amplification factors of the plurality of gain media for the light, the wavelength at which the gain becomes the maximum value can be changed. As a result, the oscillation wavelength is also variable.

Then, similarly as in the above, by temporally changing the total gain, it is also possible to temporally sweep the oscillation wavelength in the mode-lock (synchronization) state.

In a case where the maximum wavelength of the total gain is swept in the period T1 by using N pieces of gain media, in order to carry out the smooth change in the peak wavelength of the total gain, a phase difference of gains having a component of the period T1 of the gains applied to the light from the respective gain media for amplifying the adjacent frequency bands is preferably set as $2\pi/N$.

Also, in particular, in a case where the wavelength sweeping is performed at a high speed, while the time τ used for the light to propagate between the adjacent gain materials in the resonator is taken into account, it is effective to add the phase difference $2\pi\tau/T1$ to the drive of the adjacent gain media. It is however noted that in a case where the time used for the wavelength sweeping is extremely large as compared with the time used for the light to circulate in the resonator or a case where the distance between the gain materials is sufficiently close, the above-described term $2\pi\tau/T1$ may be ignored.

Also, the period of the wavelength sweeping is preferably in synchronism with the period for the light to circulate in the resonator or is preferably a reciprocal of an integer of a time used for the light to circulate one round in the resonator. By establishing the synchronism of these, when the light amplified by the total gain at a certain time point circulates in the resonator and returns to the gain medium, the light is amplified by the total gain having the same profile again, and it is therefore suppress the loss with respect to the light even when the high-speed wavelength sweeping is performed.

In the light source apparatus according to the embodiment of the present invention, in a case where the optical resonator is in the vicinity of the oscillation wavelength region and the wavelength dispersion is small or substantially 0, the frequency interval of the resonator mode basically becomes an equal interval. Therefore, as compared with the dispersion tuning system described in Non-patent Document 1, the resonator mode is excited in the wavelength region with the wider gain band, and the mode-lock can be applied.

In this case, the number of modes where the mode-lock may be performed can be increased, which contributes a stability of the mode-lock state.

Furthermore, a minimum shift amount of the oscillation wavelength in a case where the total gain is changed is equal to the FSR. In the light source apparatus according to the embodiment of the present invention, as described above, in a case where the optical resonator is in the vicinity of the oscillation wavelength region and the wavelength dispersion is small or substantially 0, the FSR does not have the wavelength dependence, and the sweeping width at the central wavelength becomes constant. Such characteristics are preferably used for the OCT light source.

As a method of stabilizing the pulse operation, a method of incorporating a supersaturated absorber in the resonator. For the supersaturated absorber, one having a nonlinear effect to absorb week light to weaken this and having a characteristic of only slightly absorbing strong light can be utilized, and as an example, saturable pigment and an element using quantum dots can be exemplified.

It is noted that a method of obtaining the mode-lock state is not limited to the above. For example, with regard to the active mode-lock, the high frequency drive signal for obtaining the mode-lock which is applied to the above-described the optical modulator may be overlapped on the control signal applied to the gain media having the plurality of amplification regions. Such a configuration where the gain media (amplifiers) and the optical modulator are combined is preferably used in the viewpoint of simplifying the optical system.

In the configuration where the gain media doubles as the optical modulator, a phase difference is also preferably added to the modulation signal which is applied to the optical gain medium for the mode-lock while the time τ for the pulse to propagate between the adjacently arranged optical gain media is taken into account. When a period of the high frequency signal applied to the optical amplifier for the mode-lock is set as T2, the phase difference of the signal components added between the adjacently arranged optical amplifiers is represented by the following expression.

$$\Delta\phi = 2\pi \times \tau / T2$$

With this addition of the phase difference, a timing at which the pulse transmits through the respective optical modulators and the time change in the amplification factors of the optical modulators can be synchronized in each of the optical modulators, the loss with respect to the light in the resonator is small, and it is possible to construct an environment where the mode-lock oscillation can be performed at a high efficiency.

In a case where the optical resonator is composed of a ring-type resonator, in particular, with regard to a case of the pulse oscillation, the resonator preferably has a length equal to or larger than a length of one pulse wave packet in the resonator. For example, in a case where a waveguide with the refractive index of 1.5 constructs the ring-type optical resonator and the modulation at 1 GHz is added to develop the mode-lock with this system, the pulse wave packet is approximately 20 cm, and the resonator length is preferably equal to or longer than this length.

In the case of the CW oscillation or the case of the mode-lock oscillation, with regard to the light source apparatus according to the embodiment of the present invention, the individual optical gain media are preferably arranged in proximity as much as possible in the ring-type optical resonator from the viewpoint of performing the high speed wavelength sweeping.

Also, in a case where the gains (amplification factors) of the plurality of optical gain media constructing the light source apparatus according to the embodiment of the present invention and the profiles have a difference, in accordance with this, by appropriately control a size or a time function of the signal (amplification current) for driving the respective optical gain media, the wavelength sweeping can be performed.

In the above, the example of using the SOAs as the optical gain medium has been described.

Next, an example of using a rare earth-added (ion doped) optical fiber as the optical gain medium will be described with reference to FIG. 16.

Figure 16:
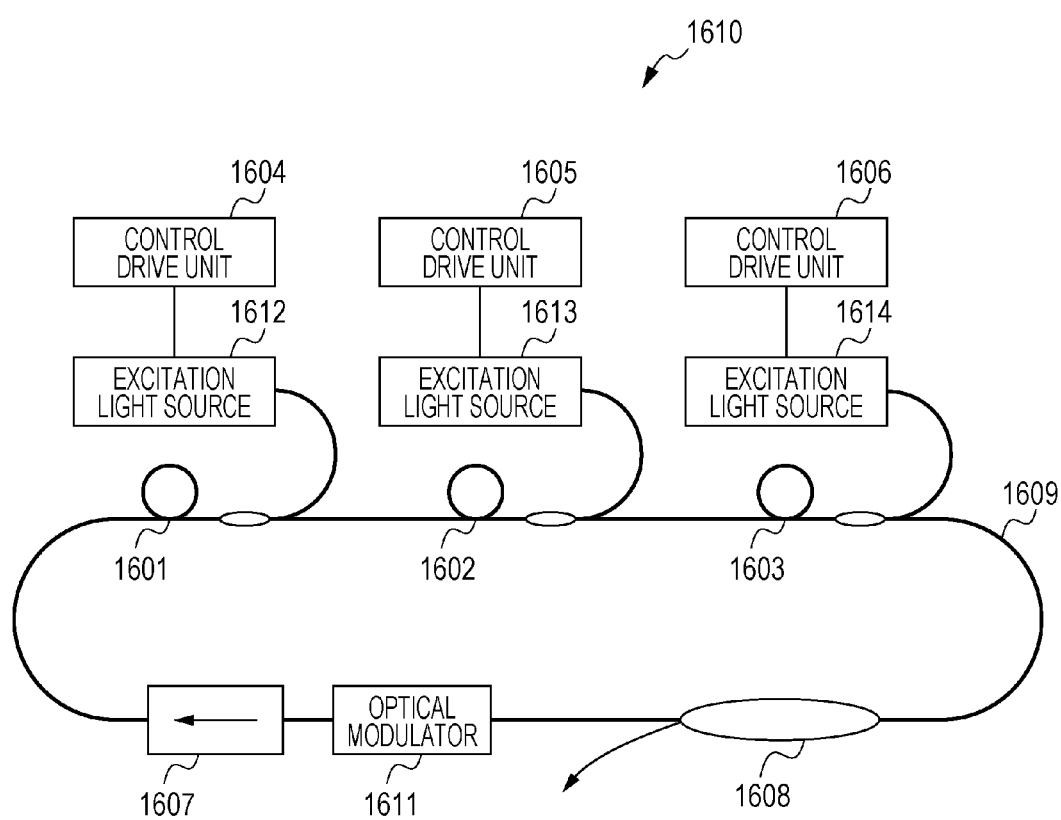
FIG. 16 is a schematic diagram illustrating an example of a light source apparatus using a rare-earth added fiber as an optical gain medium.

In FIG. 16, the optical gain media are rare-earth added fibers 1601 to 1603, and excitation light source 1612 to 1614 are optically connected to the respective rare-earth added fibers. Then, wavelengths that the respective optical gain media has at which the gain becomes the maximum value are different from each other.

Similarly, as in the case of the above-described semiconductor optical amplifier, the total gain obtained by combining the gains of the respective optical gain media is generated. Then, in order to change the profile of the total gain and the gains of the respective optical gain media, by changing intensities of excited light introduced from the excitation light source 1612 to 1614 to the rare-earth added fibers 1601 to 1603, the amplification factors that the respective rare-earth added fibers have may be changed. Also, the light emission intensities of the excitation light sources are controlled by drive signals from control drive units 1604 to 1606 that controls these excitation light sources.

In the above description, the ring-type optical resonator has been exemplified as the optical resonator for the description. As the optical resonator according to the embodiment of the present invention, a linear-type optical resonator can also be adopted other than the ring-type optical resonator.

In the case of a linear-type optical resonator, in order to have the same resonator length as the ring-type optical resonator, due to reasons that a physical length of the optical waveguide is halved, an isolator is not necessary, and the like, an inexpensive light source configuration can be realized, which is also advantageous in a miniaturization of the apparatus.

Hereinafter, specific embodiments will be exemplified to describe the present invention.

First Embodiment

CW of Wavelength-variable Light Source, Pulse Light Source

According to the present embodiment, a light source in which the oscillation wavelength can be set at a determined wavelength will be described.

Figure 7:
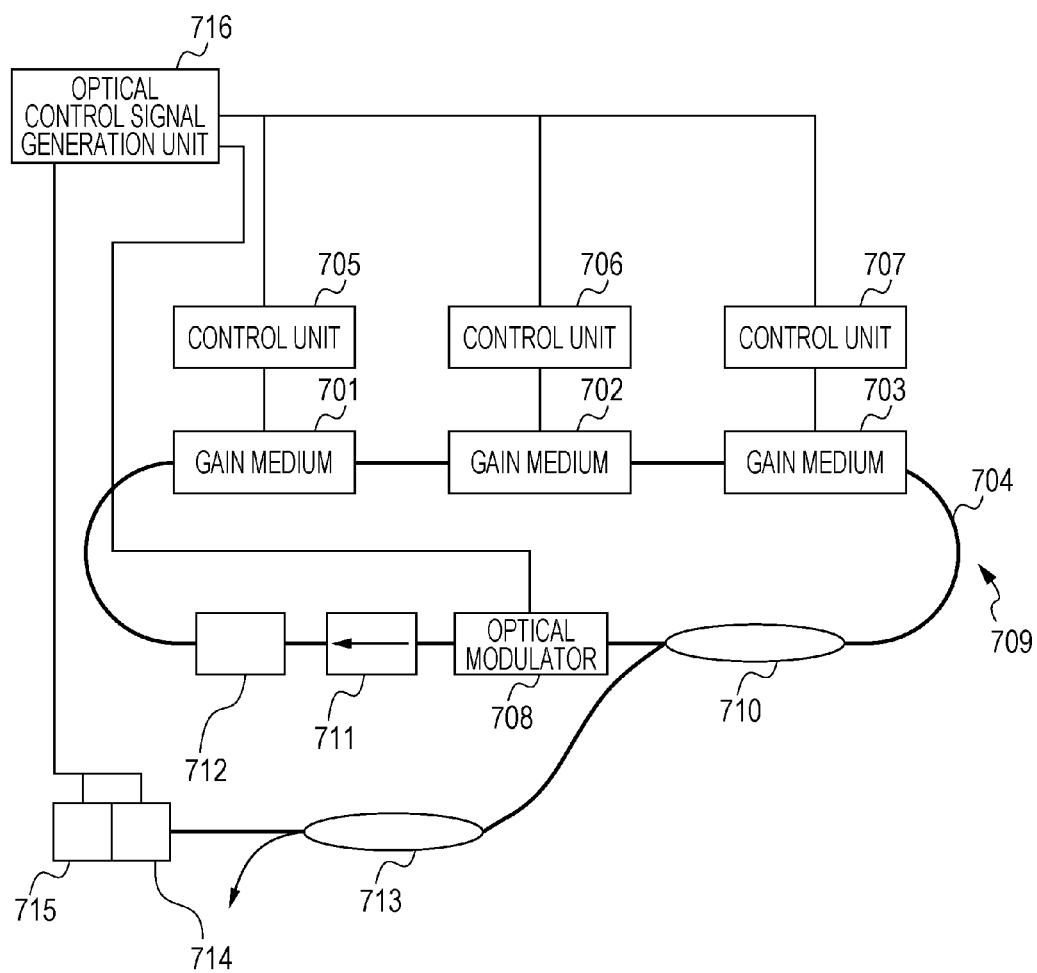
FIG. 7 is a schematic drawing for describing a light source apparatus according to a first embodiment.

FIG. 7 is a schematic diagram of the light source apparatus according to the present embodiment. In FIG. 7, an amplifier 701, an amplifier 702, and an amplifier 703 are connected in series, and a polarization maintaining fiber 704 having a length of 200 m is connected to this. A refractive index of the fiber 704 is approximately 1.5 in the vicinity of a wavelength of 1050 nm.

The polarization maintaining fiber 704 is connected to an optical modulator 708 composed of an electro-optical element via a coupler 710 having a split ratio of 9:1, and the optical modulator 708 is connected via an isolator 711 to a polarization controller 712. Then, the connection of the polarization controller 712 to the amplifier 701 constructs the ring-type resonator 709. It is noted that a polarization maintaining fiber similar to the fiber 704 is used for connecting the respective members in FIG. 7.

In the description according to the present embodiment, for the amplifiers 701, 702, and 703, the SOAs (Semiconductor Optical Amplifiers) in which the central wavelength of the gain is in the vicinity of 1050 nm are used.

To the amplifiers 701, 702, and 703, control units 705, 706, and 707 that respectively drive these amplifiers are connected. The respective control units include a DC power source and a temperature adjustment mechanism.

The light is taken out from the coupler 710 to the outside of the ring resonator 709. The taken out light is split by a coupler 713 having a split ratio of 1:1. One is utilized as an optical output, and the other one is introduced to a spectrometer 714 and a photo detector (photo diode) 715.

A signal obtained from the spectrometer 714 and the photo detector 715 is input to an optical control signal generation unit 716, and on the basis of this input signal, the signal generation unit 716 generate control signals for the control unit 705, the control unit 706, and the control unit 707 and the optical modulator 708. In other words, the optical signal output from the coupler 713 is monitored by using the spectrometer 714, the photo detector 715, and the optical control signal generation unit 716 to be subjected to a feed back control.

Figure 8:
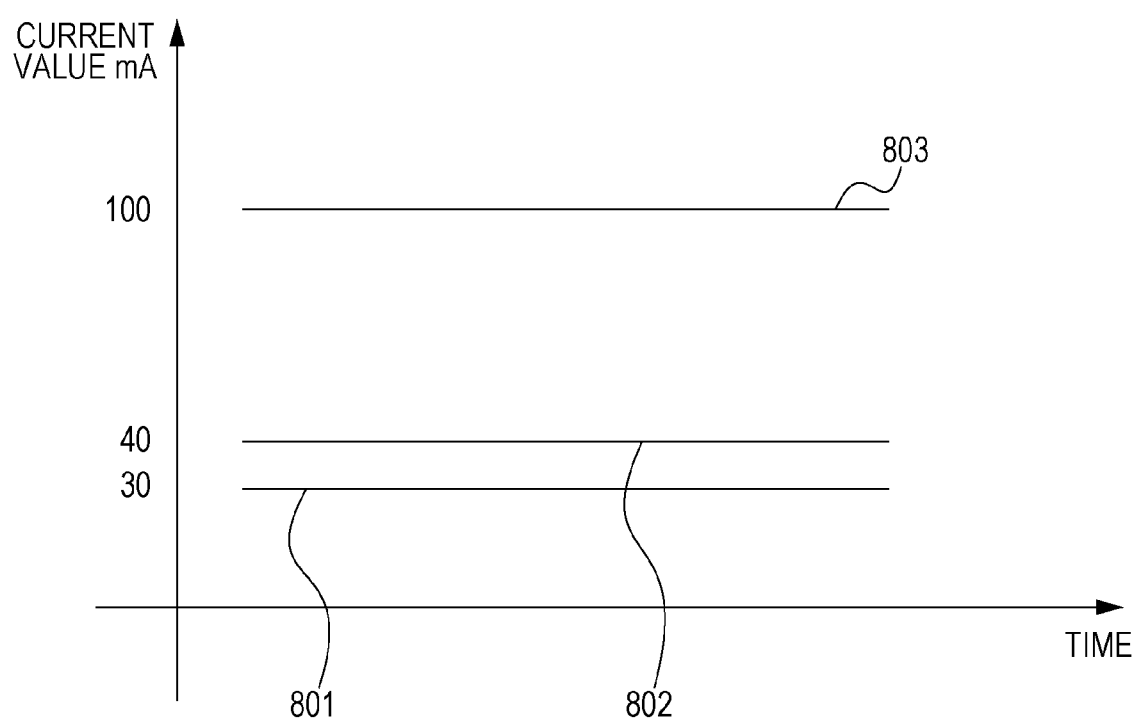
FIG. 8 is a graph representing a current value injected into an SOA according to the first embodiment.

From the control units 705, 706, and 707 that control the amplification factors of the SOAs, temporally constant-intensity current signals 801, 802, and 803 illustrated in FIG. 8 are supplied. The current signal 801 is 30 mA, the current signal 802 is 40 mA, and the current signal 803 is 100 mA.

Figure 9:
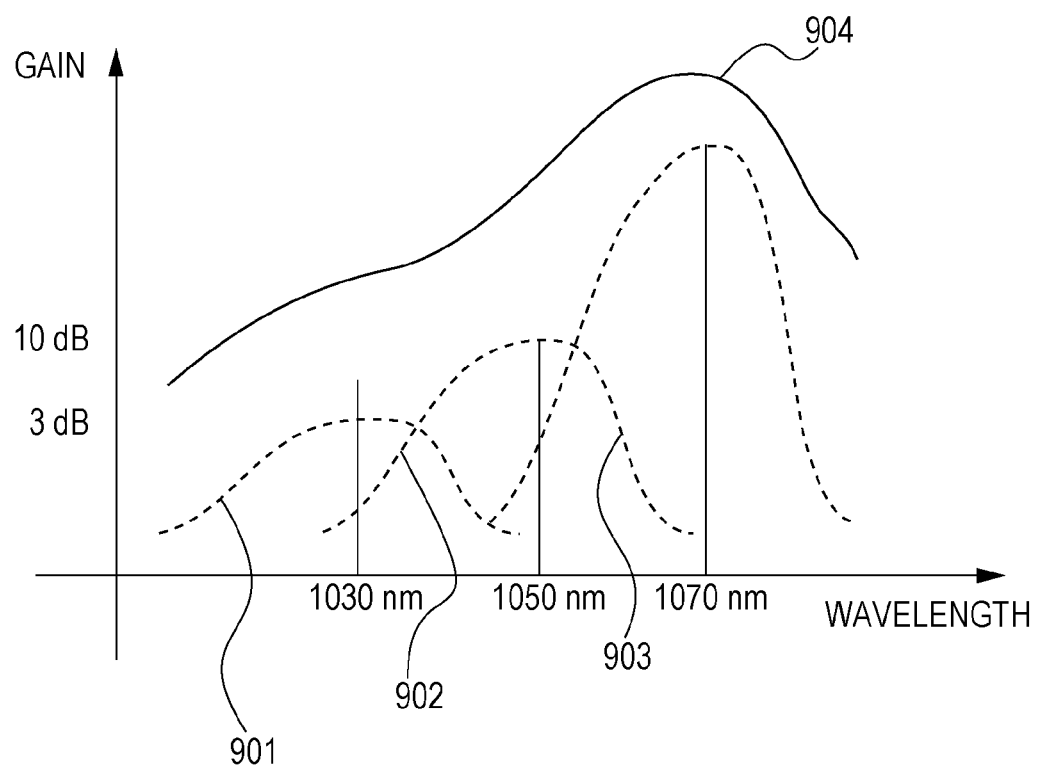
FIG. 9 is a graph representing a relation between a total gain and a spectrum according to the first embodiment.

At this time, the respective gains of the amplifiers 701, 702, and 703 are gain spectra 901, 902, and 903 illustrated in FIG. 9. The gains are respectively 3 dB, 10 dB, and 20 dB. The maximum gain wavelengths (wavelength with the maximum amplification factor) are respectively in the vicinity of 1030 nm, 1050 nm, and 1070 nm. As a result, the amplifiers 701, 702, and 703 generate a total gain 904.

According to this, light at approximately 100 mW is generated in the ring resonator.

Also, as illustrated in FIG. 8, in a case where the current injected to the SOA is stationary (constant), by regularly keeping the optical modulator 708 in the state of the maximum transmittance, the ring resonator 709 has the CW oscillation, the intensity of the taken out light is ~5 mW, and the oscillation wavelength is ~1070 nm.

Figure 10:
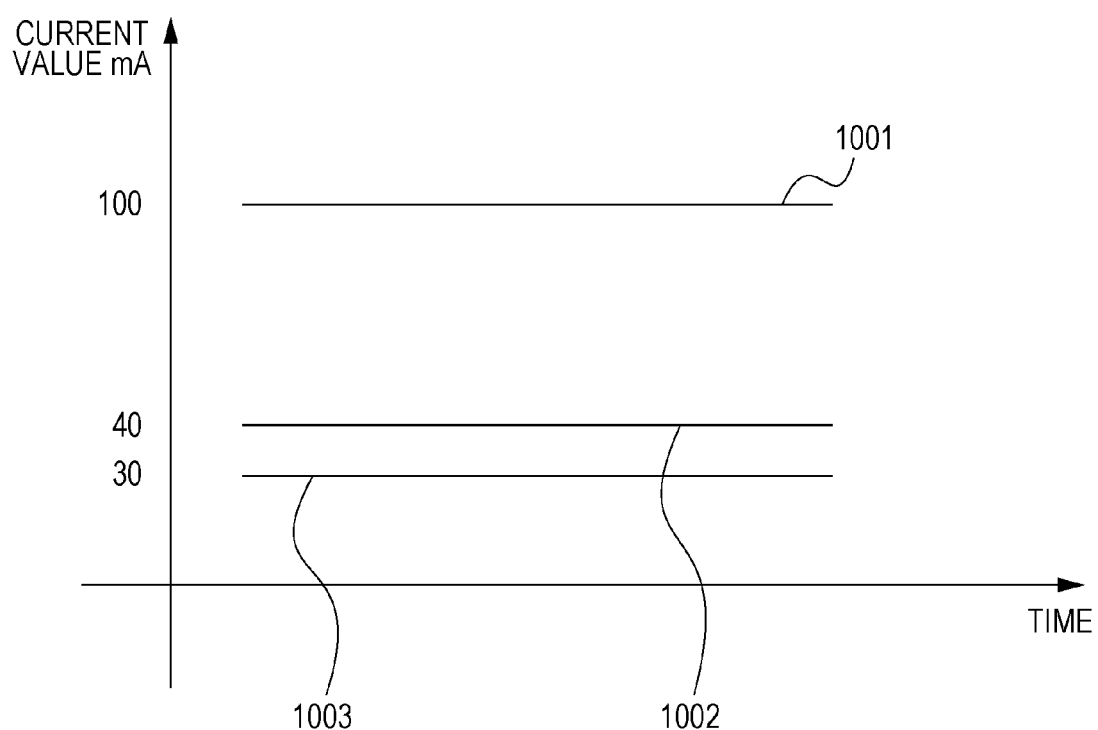
FIG. 10 is a graph representing a current value injected into the SOA according to the first embodiment.
Figure 11:
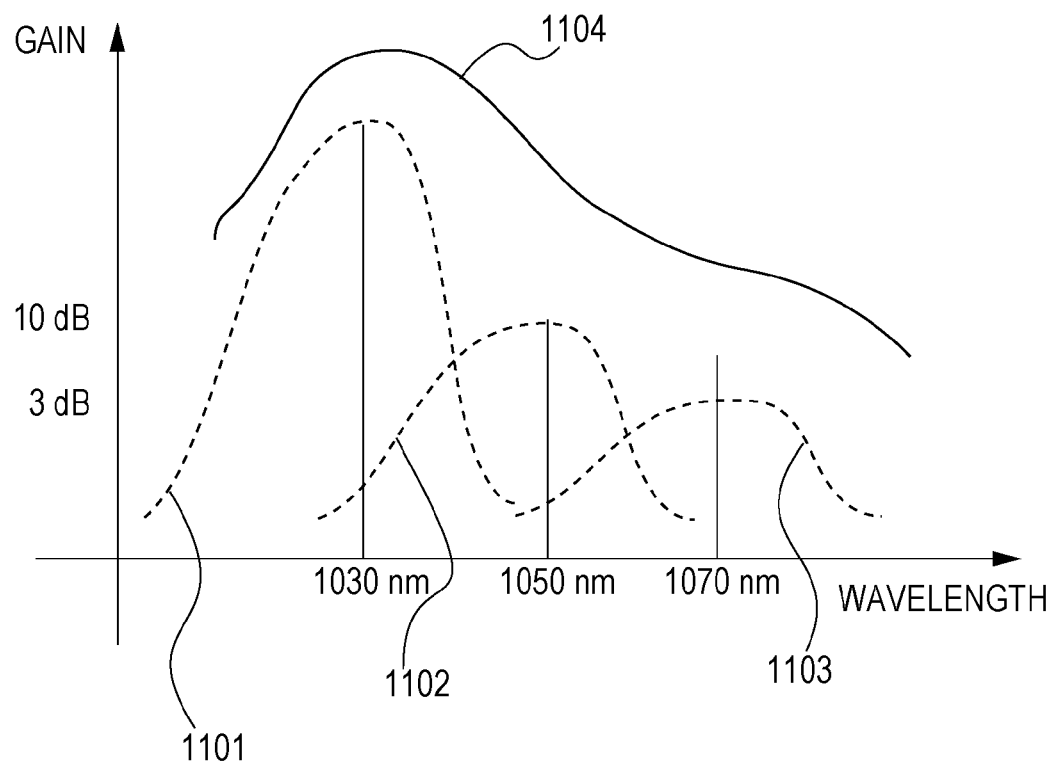
FIG. 11 is a graph representing a relation between a total gain and a spectrum according to a second embodiment.

On the other hand, when the current injected into the amplifiers 701, 702, and 703 by the control units 705, 706, and 707 are as illustrated in FIG. 10, the respective gain spectra are represented by 1101, 1102, and 1103 illustrated in FIG. 11, and a total gain 1104 is obtained. The oscillation wavelength of the CW caused by the change of the total gain becomes ~1030 nm.

In this manner, by controlling the currents injected into the respective SOAs and controlling the total gain made by the entirety of the plurality of SOAs, the CW laser can be oscillated at a desired wavelength in the gain band.

Also, in a state in which the transmittance of the optical modulator 708 is set as 0%, the spectrum of the light reaching the spectrometer 714 indicates a spectrum of the amplified spontaneous emission (ASE) that the amplifiers 701, 702, and 703 have. From this spectrum of the ASE light, the estimation on the spectrum of the total gain can be carried out. In particular, in a case where the loss of the optical system is small or a case where the wavelength dependence of the loss is small, it can be considered that the ASE spectrum almost reflects the spectrum shape of the total gain. Therefore, while the ASE spectrum is observed, it is possible to monitor the spectrum of the total gain at that time point. Furthermore, on the basis of the obtained spectrum information on the total gain, the control signals are supplied to the control units 705, 706, and 707 by the optical control signal generation unit 716, and it is also possible to set the spectrum of the total gain to have a desired shape.

Also, as another mode, the following configuration can also be adopted.

For example, the current injected into the amplifier 701, the amplifier 702, and the amplifier 703 from the control unit 705, the control unit 706, and the control unit 707 are set in a state illustrated in FIG. 8. At this time, the optical modulator is supplied with a high frequency signal. The length of the ring resonator including the polarization maintaining fiber is ~200 m, and the refractive index is ~1.5. The FSR is approximately 1 MHz. As the mode-lock frequency, the drive frequency for the optical modulator is set as 1 GHz which is 1000 times larger than the FSR, and the active mode-lock is applied. In this state, the pulse string at the repetition frequency 1 GHz is generated, and the central wavelength of the oscillation is ~1070 nm.

At this time, the resonator mode contributing to the mode synchronization is located in the band of the total gain 904 in FIG. 9.

In this state, when a balance of the currents injected from the control units 705, 706, and 707 is set as current signals 1001 to 1003 of FIG. 10, the total gain becomes the total gain 1104 of FIG. 11. Then, the central wavelength of the pulse oscillation can be set at 1030 nm.

Also, the optical amplifier (optical gain medium) itself may have the function of the optical modulator. In other words, in the above-mentioned example, the drive signal of the SOA is temporally constant and is used for deciding the total gain profile, but the high frequency signal for applying the mode-lock may be overlapped with this drive signal. In other words, instead of using the optical modulator, by modulating the amplification factor of the SOA at the high frequency at a high speed, it is also possible to apply the mode-lock.

It is noted that in the above description, the polarization maintaining fiber is used for the guide constructing the optical system, but the embodiment of the present invention is not limited to this. For example, the single mode fiber may also be used. The wavelength dispersion of the refractive index is preferably small in the target spectrum band. For example, the optical system in which the light is propagated in the air or vacuum space may also be used. Alternatively, by introducing a dispersion compensator, a dispersion compensation fiber, or the like, the wavelength dispersion in the resonator may be cancelled. The resonator length is preferably set to have a length equal to or larger than the pulse wave packet. According to the present embodiment, the length is equal to or larger than 20 cm.

According to the present embodiment, the 1050 nm band is represented as the light emission band of the SOA, but the embodiment of the present invention is not limited to this. For example, light emission in a 1.55 micron band, a 1.3 micron band, an 840 nm band, or the like can also be realized.

In the case of the 1.55 micron or 1.3 micron band, InGaAs-based, InAsP-based, and GaAsSb-based materials and the like can be adopted.

In the case of a 1.0 micron band, similarly, the InGaAs-based and GaAsSb-based materials and the like can be adopted. Also, in the case of the 840 nm band, GaAsP-based, InGaP-based, and AlGaAs-based materials and the like can be adopted.

Herein, for the gain media, the one using the SOA is represented, but a rare-earth doped fiber amplifier and the like which contains erbium, neodymium, etc., may also be used for the gain media.

With the light source according to the present embodiment, it is possible to realize a continuous oscillation light source and a pulse oscillation light source in which the central wavelength of the oscillation can be set as a desired wavelength.

Also, it is possible to realize the stable mode-lock state by suppressing the dispersion to a low level. Also, as the wavelength sweeping range is decided depending on the gain band that the respective gain media have, by taking into account the type and the number of the gain media, the setting range in the wide band can be realized.

Figure 17:
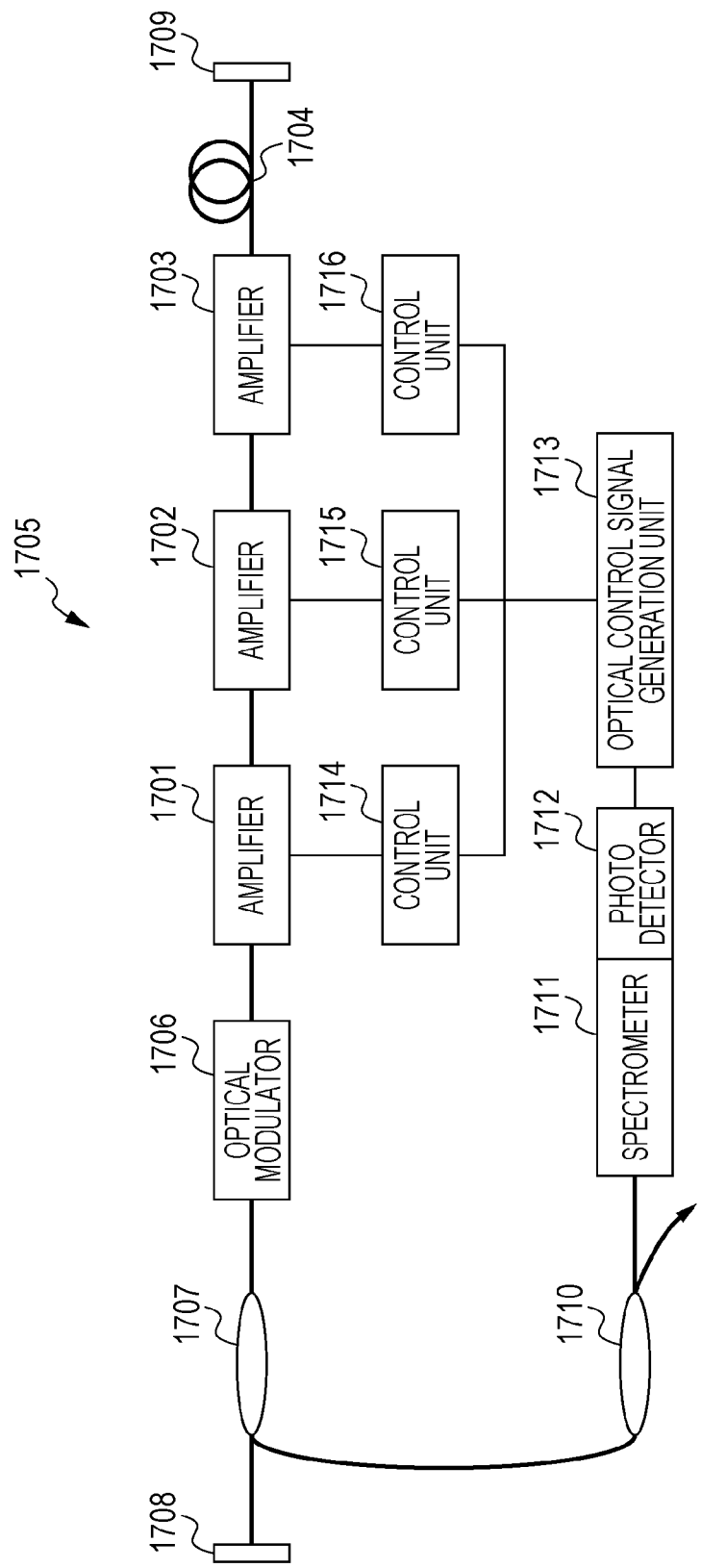
FIG. 17 is a schematic diagram for describing another example of the light source apparatus according to the present invention.

As another mode according to the present embodiment, instead of the above-described ring-type optical resonator, a linear-type optical resonator illustrated in FIG. 17 may also be adopted.

In FIG. 17, an amplifier 1701, an amplifier 1702, and an amplifier 1703 are respectively controlled via a control unit 1714, a control unit 1715, and a control unit 1716 by an optical control signal generation unit 1713.

A linear resonator 1705 is composed of an optical modulator 1706, a coupler 1707, a fiber 1704, a mirror terminal end fiber 1708, and a mirror terminal end fiber 1709 in addition to the above-described optical amplifier. The fiber 1704 may be the polarization maintaining fiber or the single mode fiber. Positions for providing the respective optical amplifiers and the polarization maintaining fiber are not limited to those illustrated above, and both may be switched with each other. Also, the respective amplifiers are preferably mutually in proximity and optically connected. A part of light taken out from the coupler 1707 is branched through a coupler 1710 to a spectrometer 1711 and a photo detector 1712. On the basis of the spectrum information obtained from the spectrometer 1711 and the photo detector 1712, the optical control signal generation unit generates the control signal, and the gain spectrum is set as a desired characteristic.

Second Embodiment

CW of the Wavelength Sweeping Light Source, Pulse Light Source

According to the present embodiment, a light source capable of temporally sweeping the oscillation wavelength will be described.

Figure 12:
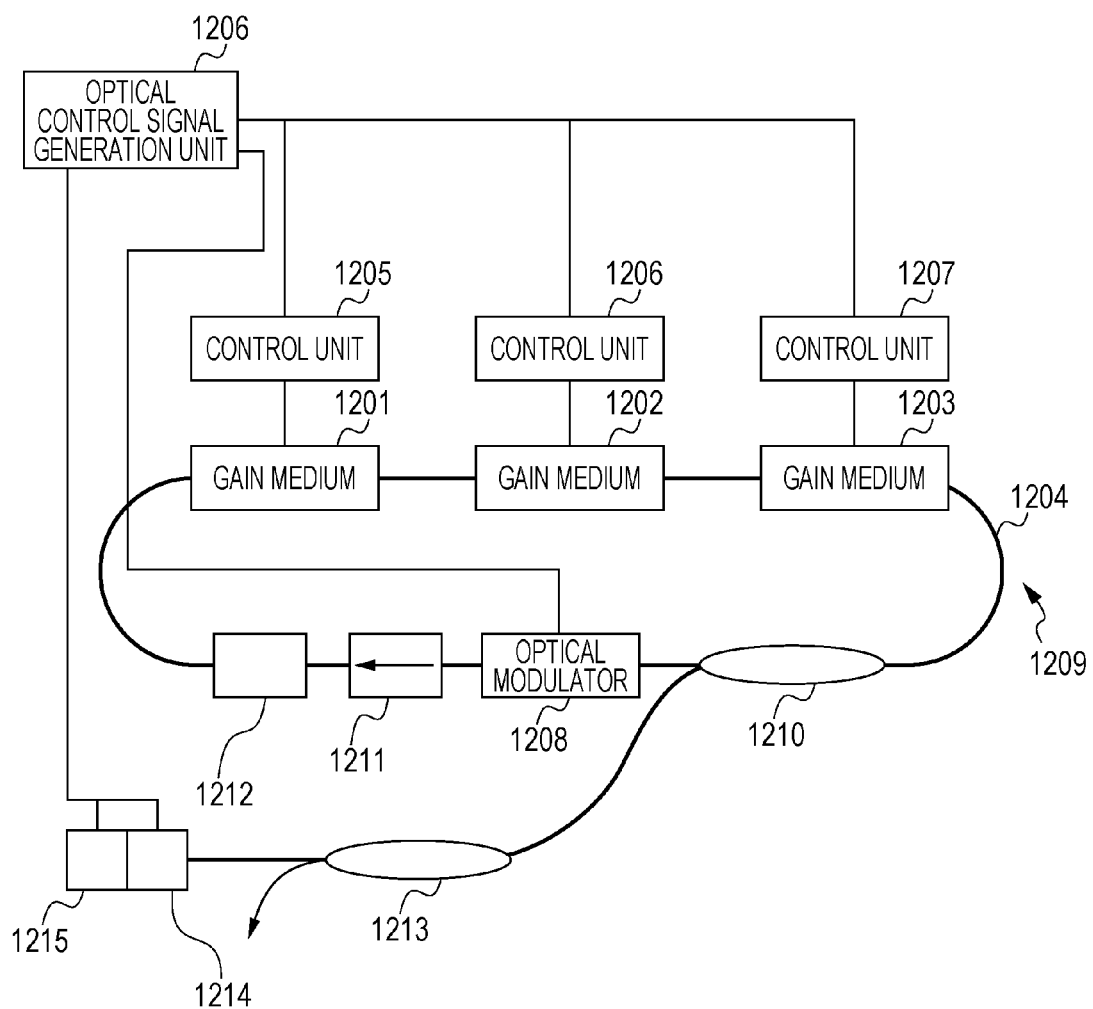
FIG. 12 is a schematic drawing for describing a light source apparatus according to the second embodiment.

FIG. 12 is a schematic diagram of the light source apparatus according to the present embodiment. In FIG. 12, an amplifier 1201, an amplifier 1202, and an amplifier 1203 are connected in series, and a polarization maintaining fiber 1204 is connected to this. An interval of the respective amplifiers is 2 m, and a length of the polarization maintaining fiber 1204 is 200 m.

A refractive index of the fiber 1204 is approximately 1.5 in the vicinity of 1050 nm.

The polarization maintaining fiber 1204 is connected to the optical modulator 1208 composed of an electro-optical element via a coupler 1210 having a split ratio of 9:1, and an optical modulator 1208 is connected via an isolator 1211 to a polarization controller 1212. Then, the connection of the polarization controller 1212 to the amplifier 1201 constructs the ring-type resonator 1209. It is noted that a polarization maintaining fiber similar to the fiber 1204 is used for connecting the respective members in FIG. 12.

In the description according to the present embodiment, for the amplifiers 1201, 1202, and 1203, the SOAs in which the gain wavelength is in the vicinity of 1050 nm are used. To the amplifiers 1201, 1202, and 1203, a control unit 1205, a control unit 1206, and a control unit 1207 that drive these amplifiers are respectively connected.

According to the present embodiment, the CW operation and the pulse operation will be described, but the optical modulator 1208 is not necessarily needed in the case of the CW operation.

The light is taken out from the coupler 1210 to the outside of the ring resonator 1209. The taken out light is split by a coupler 1213 having a split ratio of 1:1. One is utilized as an optical output, and the other one is introduced to a spectrometer 1214 and a photo detector (photo diode) 1215.

A signal obtained from the spectrometer 1214 and the photo detector 1215 is input to the optical control signal generation unit 1216, and on the basis of this input signal, the signal generation unit 1216 generates control signals for the control unit 1205, the control unit 1206, and the control unit 1207 and the optical modulator 1208. In other words, the optical signal output from the coupler 1213 is monitored by using the spectrometer 1214, the photo detector 1215, and the optical control signal generation unit 1216 to be subjected to a feed back control.

Figure 13:
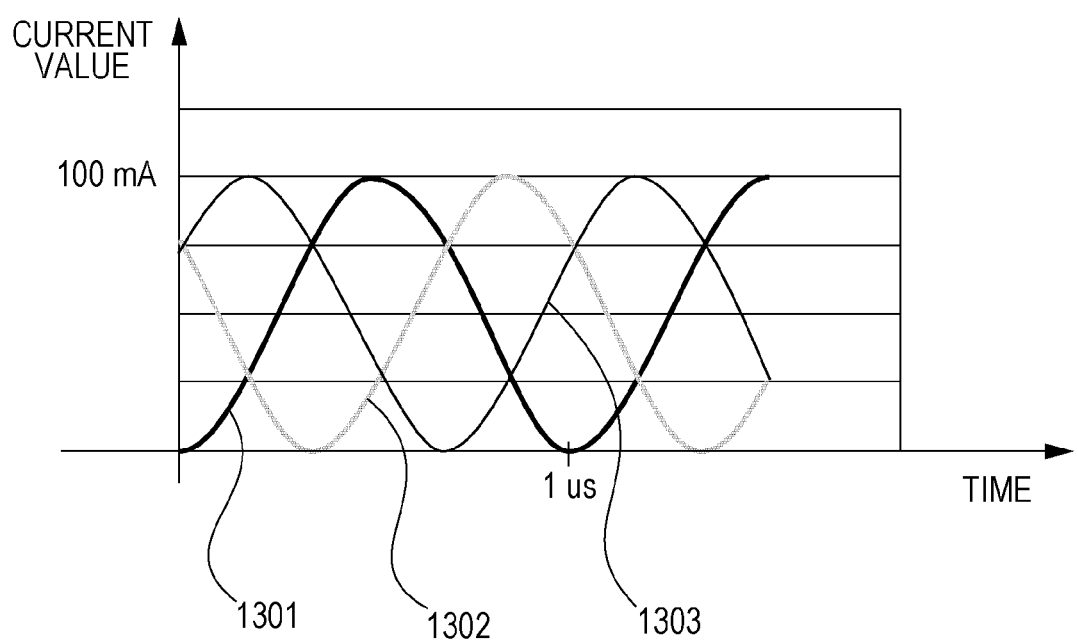
FIG. 13 is a graph representing a current value injected into the light source apparatus according to the second embodiment.

By the control units 1205, 1206, and 1207 that control the amplification factors of the SOAs, currents 1301, 1302, and 1303 illustrated in FIG. 13 are set, and the respective gains (amplification factors) of the amplifiers 1201, 1202, and 1203 temporally oscillate. This oscillation period is equivalent to the wavelength sweeping period.

Figure 14:
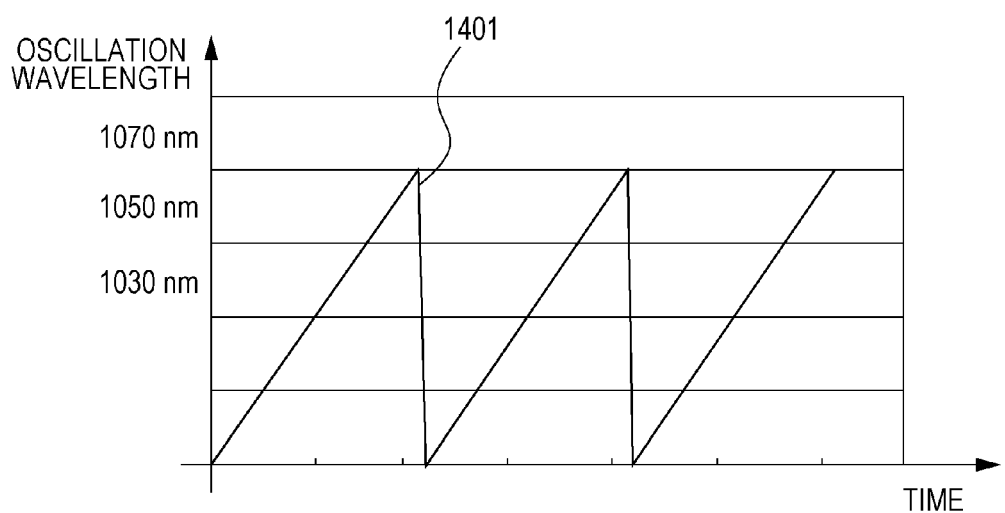
FIG. 14 is a graph representing an oscillation wavelength of the light source apparatus according to the second embodiment.

According to the present embodiment, it is assumed that the wavelength sweeping is performed at 1 kHz. As a time for the light to circulate in the resonator 1209 is approximately 1 μsec, the wavelength sweeping speed is sufficiently long as compared with the time for the light to circulate in the resonator. For this reason, the time for the light to propagate between the respective gain media is ignored, and temporal phase differences of gains given to the amplifiers 1201, 1202, and 1203 may be respectively $\frac{2}{3}\pi$ each. The wavelengths at which the amplification factors of the respective amplifiers 1201, 1202, and 1203 become the maximum values are in the vicinity of 1030 nm, 1050 nm, and 1070 nm. Then, the maximum wavelength of the total gain made from the plurality of amplifiers has a temporal fluctuation like an oscillation wavelength 1401 illustrated in FIG. 14.

According to this, light at approximately 100 mW is generated in the ring resonator 1209. Also, as illustrated in FIG. 13, if the current injected into the SOA temporally fluctuates and the optical modulator 1208 is regularly set in the state of the maximum transmittance, the ring resonator 1209 has the CW oscillation, and the oscillation wavelength is swept in a range from 1030 nm to 1070 nm.

In this manner, by controlling the currents injected into the respective SOAs and performing a control so as to temporally fluctuate the total gain made by the entirety of the plurality of SOAs, it is possible to sweep the laser oscillation wavelength of the CW light in the gain band.

Also, in a state in which the transmittance of the optical modulator 1208 is set as 0%, the spectrum of the light reaching the spectrometer 1214 represents a spectrum of the ASE light (amplified spontaneous emission light) that the amplifiers 1201, 1202, and 1203 have. From this spectrum of the ASE light, the estimation on the spectrum of the total gain can be performed. In particular, in a case where the loss of the optical system is small or a case where the wavelength dependence of the loss is small, it can be considered that the ASE spectrum almost reflects the spectrum shape of the total gain. Therefore, while the ASE spectrum is observed, it is possible to monitor the spectrum of the total gain at that time point. Furthermore, on the basis of the obtained spectrum information on the total gain, the control signals are supplied from the optical control signal generation unit 1216 to the control units 1205, 1206, and 1207, and it is also possible to set the spectrum of the total gain to have a desired shape.

Also, in the configuration according to the present embodiment, when the wavelength at which the gain becomes the maximum value is temporally changed, the period is preferably matched with the time for the light to circulate in the resonator or set as an integral multiple of this. In this case, the Fourier domain mode-lock operation is realized where the wavelength at which the intensity becomes the maximum value is amplified as the ASE light changing with time circulates in the optical resonator.

In the present configuration, as the speed at which the light circulates in the resonator is 1 μs, the above-described wavelength at which the gain becomes the maximum value may be changed to 1 μs or an integral multiple of this.

Also, as the interval between the respective gain media is 2 m, when a refractive index of the polarization maintaining fiber is set as 1.5, the time for the light to propagate between the respective gain media is 10 ns, and the temporal phase differences of the gains provided by the amplifiers 1201, 1202, and 1203 may be respectively $\frac{2}{3}\pi + 2\pi \times 10^{-8}/10^{-6}$ each.

By performing such a drive, it is possible to construct the FDML light source in which the central wavelength changes at a period of 1 μs.

Also, as another mode, the following configuration can also be adopted.

For example, by using the control units 1205, 1206, and 1207, a control is performed so that currents injected into the gain media 1201, 1202, 1203 respectively become currents 1301, 1302, and 1303 illustrated in FIG. 13. Herein, the currents 1301, 1302, and 1303 indicate sine curves (curved lines) whose phases are respectively shifted. In this manner, by temporally changing the currents injected into the respective gain media, the total gain obtained by these gain media changes.

At this time, the optical modulator 1208 is supplied with the high frequency signal. When the length of the ring resonator including the polarization maintaining fiber 1204 is set as ~200 m and the refractive index is set as ~1.5, the optical circumferential length of the ring resonator is approximately 300 m. Thus, the light propagating therein circulates at ~1 MHz in the resonator. Therefore, the FSR of this resonator is also ~1 MHz. In view of the above, by setting the drive frequency for the optical modulator as 1 MHz or an integral multiple of this, the mode-lock (synchronization) is obtained.

In view of the above, according to the present embodiment, in order to realize the mode-lock, the high frequency signal at 1 GHz is applied to the optical modulator 1208. According to this, in the ring resonator, 1000 optical pulse crests circulate at the same time. Therefore, in this state, the pulse string at the repetition frequency 1 GHz is generated, and also the maximum wavelength of the total gain changes with time. Thus, the wavelength region where the mode-lock is applied temporally changes. According to this, the central wavelength of the oscillation can be swept in a range from 1030 nm to 1070 nm.

When the wavelength sweeping frequency is set as 1 MHz, a distance between the respective gain media is 2 m and 3 m in terms of an optical path, and thus the time for the light to propagate therebetween is 10 ns. By taking this state into account, the wavelength sweeping signal at 1 MHz is added with a correction signal. In other words, a phase difference of the signal components applied to the mutual respective gain media is preferably set as $\frac{2}{3}\pi + 2\pi \times 10^{-2}$ in the case of the present embodiment.

Also, the SOA (semiconductor optical amplifier) have the function of the optical modulator. In the above-mentioned example, the drive signal of the SOA temporally changes. The signal is for the wavelength sweeping and also is used for deciding the total gain profile. However, the high frequency signal for applying the mode-lock may be overlapped with this signal. In other words, instead of using the optical modulator, by modulating the amplification factor of the SOA at the high frequency at a high speed, it is also possible to apply the mode-lock.

In that case, similarly as in the above, in a case where a phase difference between the high frequency signals for the mode-lock which are applied to the gain materials adjacently arranged in the resonator is 10 ns, a phase difference in a case where the mode-lock is applied by the high frequency signal at 1 GHz may be set as $2\pi \times 10$.

In the description according to the present embodiment, the polarization maintaining fiber is used for the optical waveguide constructing the optical system, but the optical waveguide is not limited to this. For example, the single mode fiber may also be used. The wavelength dispersion of the refractive index is preferably small in the target spectrum band. By introducing a dispersion compensator, a dispersion compensation fiber, or the like, the wavelength dispersion in the resonator may be cancelled, and in principle, the optical system in which the light is propagated in the air or vacuum space may also be adopted.

In a case where the wavelength dispersion does not exist or is extremely small, even during the wavelength sweeping, the change in the FSR caused by the change of the central wavelength becomes small to be negligible. For this reason, it is not necessary to change the drive frequency of the high frequency signal applied to the optical modulator for inducing the mode-lock or the SOA, the configuration of the light source apparatus becomes preferably simplified.

The resonator length is preferably set to have a length equal to or larger than the pulse wave packet. With the light source according to the present embodiment, it is possible to realize the pulse oscillation light source or the continuous oscillation light source capable of temporally sweeping the central wavelength of the oscillation at a high speed. Also, it is possible to realize the stable mode-lock state by suppressing the dispersion to a low level. As the wavelength sweeping range is decided depending on the gain band that the respective gain media have, by taking into account the type and the number of the gain media, the setting range in the wide band can be realized.

Figure 18:
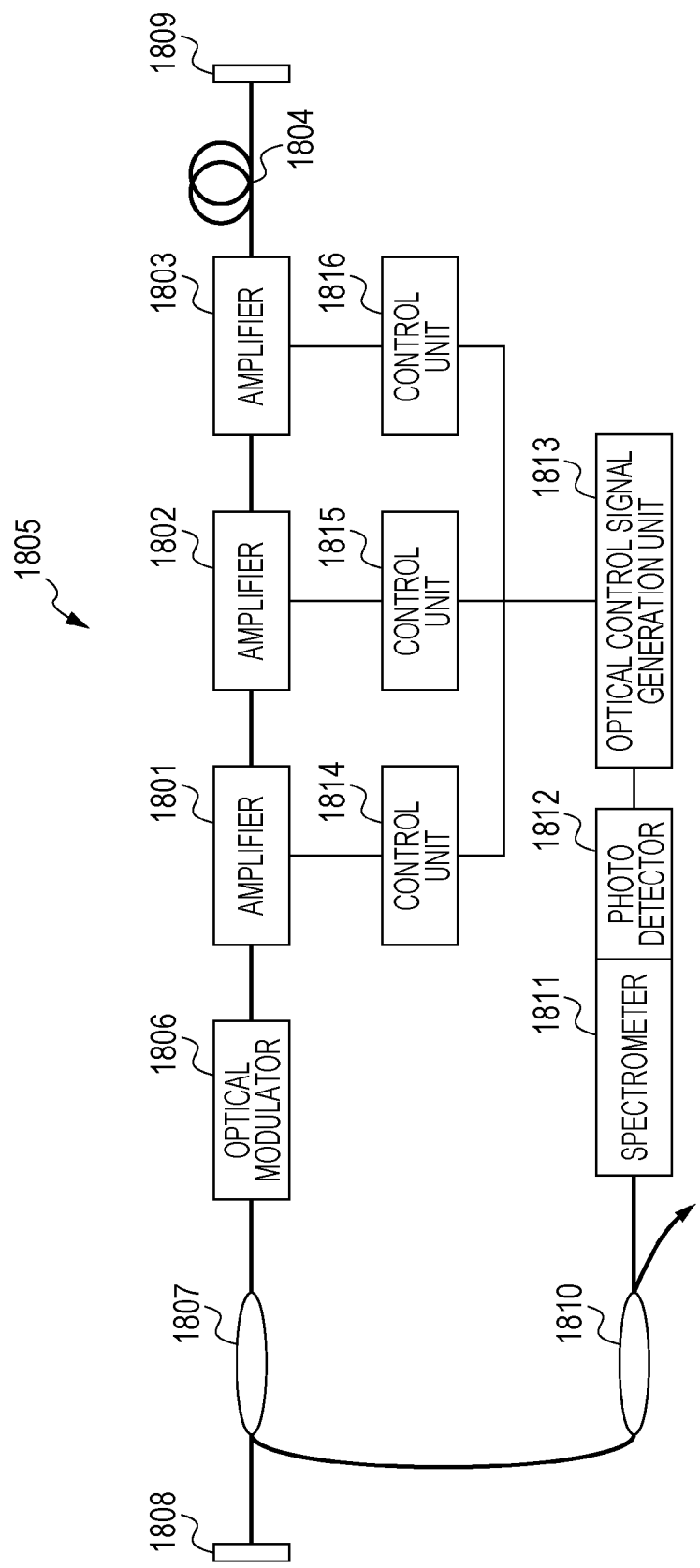
FIG. 18 is a schematic diagram for describing another example of the light source apparatus according to the present invention.

As another mode according to the present embodiment, an case is exemplified in which for the optical resonator, a linear-type optical resonator illustrated in FIG. 18 is adopted, for example, instead of the above-described ring-type resonator.

In FIG. 18, an amplifier 1801, an amplifier 1802, and an amplifier 1803 are respectively controlled via a control unit 1814, a control unit 1815, and a control unit 1816 from the optical control signal generation unit 1813.

A linear resonator 1805 is composed of an optical modulator 1806, a coupler 1807, a fiber 1804, a mirror terminal end fiber 1808, and a mirror terminal end fiber 1809 in addition to the above-described optical amplifier. The fiber 1804 may be the polarization maintaining fiber or the single mode fiber.

A part of light taken out from the coupler 1807 is branched through a coupler 1810 to a spectrometer 1811 and a photo detector 1812. On the basis of the spectrum information obtained from the spectrometer 1811 and the photo detector 1812, as the optical control signal generation unit generates the control signal, the gain spectrum is set to have a desired characteristic.

Third Embodiment

An embodiment of a tomographic image pickup apparatus (OCT apparatus) using the light source according to the embodiment of the present invention will be illustrated.

Figure 15:
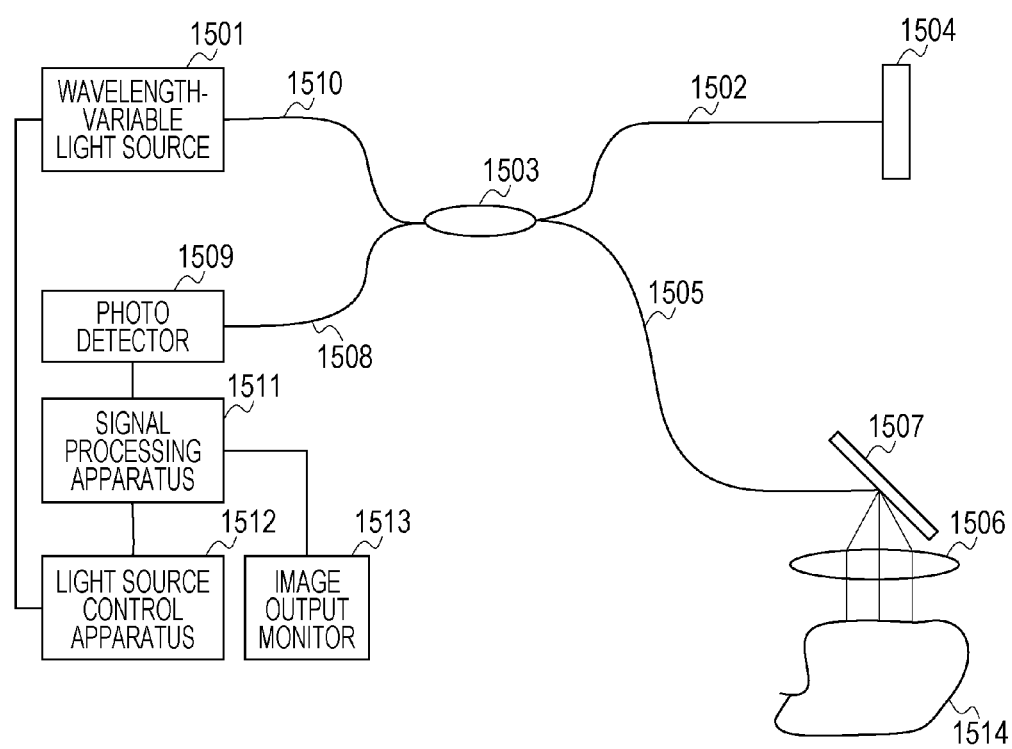
FIG. 15 is a schematic drawing of an OCT apparatus constituted by using the light source apparatus according to the present invention.

FIG. 15 is a schematic diagram of an OCT apparatus according to the present embodiment. The OCT apparatus of FIG. 15 is basically composed of a light source unit (1501, etc.), a sample measurement unit (1507, etc.) configured to irradiate a sample with light from the light source unit and transmit reflected light from a sample part, a reference unit configured to irradiate a reference mirror with the light and transmit reflected light from the reference mirror (1502, etc.), an interference unit configured to interfere two reflected lights (1503), a light detection unit configured to detect interference light obtained by the interference unit (1509, etc.), and an image processing unit configured to perform an image processing on the basis of the light detected by the light detection unit (for obtaining a tomographic image) (1511). Hereinafter, a description will be provided of the respective components.

The light source unit is composed by including a wavelength-variable light source 1501 and a light source control unit 1512 configured to control the wavelength-variable light source. The wavelength-variable light source 1501 is connected via the optical fiber 1510 for the light irradiation to a fiber coupler 1503 constituting the interference unit.

A reflection mirror 1504 is connected to a reference light optical path fiber 1502 to constitute the reference unit, and the fiber 1502 is connected to the fiber coupler 1503.

An inspection light optical path fiber 1505, an irradiation condenser optical system 1506, and an irradiation position scanning mirror 1507 constitute the measurement unit, and the inspection light optical path fiber 1505 is connected to the fiber coupler 1503. In the fiber coupler 1503, backscattered light generated from an internal part and a surface of an inspection object 1514 is interfered with return light from the reference unit to become the interference light.

The light detection unit is composed of a light receiving fiber 1508 and a photo detector 1509 and is configured to guide the interference light generated in the fiber coupler 1503 to the photo detector 1509.

The light received by the photo detector 1509 is converted into a spectrum signal by the signal processing apparatus 1511 and is further subjected to Fourier transform to obtain depth information on the inspected object. The obtained depth information is displayed on an image output monitor 1513 as a tomographic image.

Herein, the signal processing apparatus 1511 can be composed of a personal computer or the like, and the image output monitor 1513 can be composed of a display screen of the personal computer or the like.

A characteristic according to the present embodiment resides in the light source unit, and the oscillation wavelength, the intensity, and the time change of the wavelength-variable light source 1501 are controlled by the light source control apparatus 1512.

The light source control apparatus 1512 is connected to the signal processing apparatus 1511 that also controls a drive signal and the like for the irradiation position scanning mirror 1507 and is in synchronism with a drive of the scanning mirror 1507 to control the wavelength-variable light source 1501.

For example, when the light source apparatus described according to the second embodiment is used as the wavelength-variable light source 1501 according to the present embodiment, this light source apparatus can perform the wavelength sweeping in a wide band at a high speed. Therefore, it is possible to obtain tomographic image information at a high speed in which a depth resolution is a high resolution. This OCT apparatus is useful for a tomographic image pickup in eye clinics, dental clinics, dermatological clinics, and the like.

The light source apparatus according to the embodiment of the present invention can be utilized in fields where the wavelength-variable light source can be applied such as the communication network field and the field of the inspection apparatus.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2009-279912 filed Dec. 9, 2009, which is hereby incorporated by reference herein in its entirety.

What is claimed is:

1. A light source apparatus comprising:
an optical resonator including a plurality of gain media that amplify light and an optical waveguide; and
a control unit configured to individually control amplification factors of the plurality of gain media,
wherein the plurality of gain media have mutually different maximum gain wavelengths whose amplification regions are mutually partially overlapped, and a wavelength at which a total gain by the plurality of gain media becomes a maximum value is set to be variable on the basis of the control on the amplification factors,
wherein the light source apparatus emits light having the wavelength at which the total gain becomes the maximum value,
wherein the optical resonator is a ring-type optical resonator~
wherein the plurality of gain media is provided in series and in a state of being distant from each other, and
wherein the control unit is configured to individually control a time change in the amplification factor of each gain medium according to a period of time necessary for propagating the light between each gain medium among the plurality of gain media,
wherein, in a case where a sweeping period of the wavelength at which the total gain is the maximum value is set as T1 and where a time necessary for propagating the light between each gain medium among the plurality of gain media is set as z, the control unit is configured to change the amplification factor of each of the plurality of gain media so that a phase difference in time changes in the amplification factors of successive gain media satisfies $2\pi \times \tau / T1$.

2. The light source apparatus according to claim 1, wherein the amplification factors of the plurality of gain media are temporally periodically fluctuated.

3. The light source apparatus according to claim 2, wherein a magnitude of the total gain by the plurality of gain media is temporally periodically fluctuated.

4. The light source apparatus according to claim 1, wherein the period of a wavelength sweeping is a reciprocal of an integer of a time used for the light at the wavelength to circulate in the ring-type optical resonator to circulate one round in the ring-type optical resonator.

5. The light source apparatus according to claim 1, wherein a phase difference $\Delta\phi$ of signal components having a period T1 among time changes in amplification factors of gain media having adjacent amplification regions among the plurality of gain media satisfies the following expression when a total number of the gain medium is set as N, a time for the light to circulate in the ring-type optical resonator to propagate between each gain medium among the plurality of gain media is set as $\tau$, and T1 denotes a period of a wavelength sweeping:

$$\Delta\phi = 2\pi/N + 2\pi \times \tau / T1.$$

6. The light source apparatus according to claim 1, wherein the gain medium is a semiconductor optical amplifier.

7. The light source apparatus according to claim 6, wherein the semiconductor optical amplifier is one using a material selected from a group including an InGaAs-based material, a GaAsSb-based material, an InAsP-based material, a GaAsP-based material, an InGaP-based material, and an AlGaAs-based material.

8. The light source apparatus according to claim 1, wherein the gain medium is a rare-earth ion-doped optical fiber.

9. The light source apparatus according to claim 1, wherein the gain medium is fluorescence pigment.

10. The light source apparatus according to claim 1, wherein the optical waveguide is composed of a polarization maintaining fiber.

11. The light source apparatus according to claim 1, wherein the optical waveguide is composed of a single mode fiber.

12. The light source apparatus according to claim 1, wherein the ring-type optical resonator includes an optical modulator.

13. The light source apparatus according to claim 12, wherein a frequency for driving the optical modulator is equal to an integral multiple of a free spectral range that the ring-type optical resonator has.

14. The light source apparatus according to claim 12, wherein the optical modulator doubles as the gain medium.

15. The light source apparatus according to claim 14, wherein when a period of high frequency signals applied to each gain medium among the plurality of gain media is set as T2 and a time for the light to circulate in the ring-type optical resonator to propagate between each gain medium among the plurality of gain media is set as $\tau$, a phase difference $\Delta\phi$ of the signals applied to successive gain media satisfies the following expression:

$$\Delta\phi = 2\pi \times \tau / T2.$$

16. The light source apparatus according to claim 14, wherein a length of the ring-type optical resonator is longer than a length of a wave packet of the light pulse circulating in the ring-type optical resonator.

17. The light source apparatus according to claim 1, wherein the optical waveguide has a group velocity dispersion of zero with respect to the wavelength of the amplification regions of the plurality of gain media.

18. The light source apparatus according to claim 12, further comprising a unit configured to monitor a wavelength or an intensity of light output from the ring-type optical resonator and send a control signal to the control unit or the optical modulator.

19. The light source apparatus according to claim 18, wherein a spectrum of amplified spontaneous emission light output from the gain medium is monitored, and the total gain is adjusted by using the signal.

20. An optical coherence tomographic apparatus comprising:
a light source unit using the light source apparatus according to claim 1;
a sample measurement unit configured to irradiate a sample with light from the light source unit and transmit reflected light from the sample;
a reference unit configured to irradiate a reference mirror with the light from the light source unit and transmit reflected light from the reference mirror;
an interference unit configured to interfere the reflected light from the sample measurement unit and the reflected light from the reference unit;

a light detection unit configured to detect interference light from the interference unit; and an image processing unit configured to obtain a tomographic image of the sample on the basis of light detected by the light detection unit.

21. The light source apparatus according to claim 1, wherein a shape of the total gain has a single peak property.

22. The light source apparatus according to claim 1, wherein the wavelength of the emitting light is temporally swept.

23. The light source apparatus according to claim 1, wherein the wavelength of the light emitted from the light source apparatus is swept in a range from 1030 nm to 1070 nm.

24. The light source apparatus according to claim 1, wherein a number of the plurality of gain media is equal to or more than three and equal to or less than five.

25. The light source apparatus according to claim 1, further comprising a current source configured to inject currents into the plurality of gain media, and a delay circuit configured to introduce a phase difference to a time change in the amplification factor of each of the plurality of gain media by adding, to current signals of the currents, phase differences different from each other between the plurality of gain media to differentiate a delay amount.

* * * * *